United States Patent [19]

Niedballa et al.

[11] Patent Number: 5,284,647
[45] Date of Patent: Feb. 8, 1994

[54] MESOTETRAPHENYLPORPHYRIN COMPLEX COMPOUNDS, PROCESS FOR THEIR PRODUCTION AND PHARMACEUTICAL AGENTS CONTAINING THEM

[75] Inventors: Ulrich Niedballa; Hanns-Joachim Weinmann; Heinz Gries; Jürgen Conrad; Sabina Hofmann; Ulrich Speck, all of Berlin, Fed. Rep. of Germany

[73] Assignee: Schering Aktiengesellschaft, Berlin and Bergkamen, Fed. Rep. of Germany

[21] Appl. No.: 817,892

[22] Filed: Jan. 9, 1992

Related U.S. Application Data

[63] Continuation-in-part of Ser. No. 325,324, Mar. 17, 1989, abandoned.

[30] Foreign Application Priority Data

Mar. 18, 1988 [DE] Fed. Rep. of Germany .... 3809671.4

[51] Int. Cl.$^5$ ............... A61K 31/555; A61K 31/40; G01N 24/08
[52] U.S. Cl. ...................... 424/81; 514/185; 514/322; 514/365; 514/372; 514/374; 514/378; 514/385; 514/397; 514/222.2; 514/226.8; 514/227.8; 514/232.5; 540/145; 534/14; 534/15; 534/16; 128/653.4
[58] Field of Search ............... 514/185, 322, 365, 372, 514/374, 378, 385, 397, 403, 410, 222.2, 226.8, 227.8, 232.5, 255, 256; 424/9; 534/14, 15, 16; 540/145

[56] References Cited

U.S. PATENT DOCUMENTS

| | | | |
|---|---|---|---|
| 4,614,723 | 9/1986 | Schmidt et al. | 540/145 |
| 4,804,529 | 2/1989 | Bardy et al. | 424/9 |
| 4,986,256 | 1/1991 | Cohen et al. | 9/ |

FOREIGN PATENT DOCUMENTS

0066884 6/1982 European Pat. Off. .
2566776 of 0000 France .

OTHER PUBLICATIONS

Kessel et al. Chemical Abstracts, vol. 107, 1987 Abstract 111877p.
Halperm Magn. Rosan Mol. 1987 5(3) 302-5 Chemical Abstracts, vol. 107, 1987, Abs. 194281p.
Cooper, Spectroscopic Techniques for Organic Chemists, (J. Wiley and Sons, New York, 1980) pp. 105 to 117.
Yizhen et al., "The Synthesis of Two Monosubstituted meso-Tetraphenylporphine Sulfonates", J. Heterocyclic Chem., 23, 1565 (1986).
Patent Abstracts of Japan, vol. 12, No. 373, Oct. 6, 1988, 68126880.
D. Kessel et al., "Tumor-localizing Components of the Porphyrin Preparation Hematoporphyrin Derivative", Cancer Research 43, 1994-1999 (May 1983).
N. J. Patronas et al., "Metalloporphyrin Contrast Agents for Magnetic Resonance Imaging of Human Tumors in Mice", Cancer Treatment Reports, vol. 70, No. 391-396 (Mar. 1986).

(List continued on next page.)

Primary Examiner—John M. Ford
Assistant Examiner—P. K. Sripada
Attorney, Agent, or Firm—Millen, White, Zelano, & Branigan

[57] ABSTRACT

Porphyrin complex compounds, consisting of a meso-tetraphenylporphyrin ligand, optionally at least one ion of an element with atomic numbers 13, 21, 32, 37-39, 42-44, 49, 50 or 57-83 as well as optionally cations of inorganic and/or organic bases, amino acids or amino acid amides, are valuable diagnostic and therapeutic agents.

33 Claims, No Drawings

OTHER PUBLICATIONS

Zanelli et al., "Synthetic Porphyrins as Tumour-Localizing Agents," British Journal of Radiology, 54, pp. 403–407 (1981).

Winkelman et al., The Concentration in Tumor and Other Tissues of Parenterally Administered Tritium- and C-labeled Tetraphenylporphinesulfonate, Cancer Research 27, Part 1, 2060–2064, Nov. 1967.

Ni et al., Solvent and Substituent Effects on the Electron-Transfer Rate Constants . . . , Inorganic Chemistry, vol. 17, No. 2, (1978) pp. 228–231.

Kadish et al., Rate Constants of Substituted Iron meso-Tetraphenylporphrins, Journal of the Am. Chem. Soc./98:26/Dec. 22, 1976, pp. 8387–8390.

Adler, Alan D., A Simplified Synthesis for meso-Tetraphenylporphin, J. Org. Chem., 32, p. 476 (1967).

Fournari et al., Journal of Org. Chem., 110 (1976) 205–17.

Grant & Hackh's Chemical Dictionary, 5th edition, copyright 1987 Roger L. Grant, Claire Grant,; p. 53.

Cohen et al., "Metalloporphyrins as Potential Contrast Agents in Magnetic Resonance Imaging," Contrast Agents in Magnetic Resonance Imaging, Proceedings of International Workshop, 1986, pp. 35–40.

Datta-Gupta et al., "Synthetic Porphyrins. I. Synthesis and Spectra of some para-Substituted meso-Tetraphenylporphines," Journal of Heterocyclic Chemistry, 3, pp. 495–502 (1966).

MESOTETRAPHENYLPORPHYRIN COMPLEX COMPOUNDS, PROCESS FOR THEIR PRODUCTION AND PHARMACEUTICAL AGENTS CONTAINING THEM

This application is a continuation-in-part of application Ser. No. 07/325,324, filed Mar. 17, 1989, now abandoned.

BACKGROUND OF THE INVENTION

The invention relates to mesotetraphenylporphyrin complex compounds, new pharmaceutical agents containing these compounds, their use in diagnosis and therapy and processes for the production of these compounds and agents.

The use of complexing agents or complexes or their salts in medicine has been known for a long time. The following are examples:

Complexing agents as stabilizers of pharmaceutical preparations, complexes and their salts as adjuvants for the administration of poorly soluble ions (e.g., iron), complexing agents and complexes (preferably calcium or zinc), optionally as salts with inorganic and/or organic bases, as a poison antidote in the case of inadvertent incorporation of heavy metals or their radioactive isotopes and complexing agents as adjuvants in nuclear medicine using radioactive isotopes such as $^{99m}Tc$ for radionuclide imaging are known.

In patents EP 71564, EP 130934 and DE-OS 3401052, recently complexes and complex salts have been presented as diagnostic agents, primarily as NMR diagnostic agents.

These complexes and complex salts are tolerated quite well and guarantee as complete an excretion of the ions as possible. But they still do not optimally fulfill all criteria that determine the relative effectiveness of an NMR contrast medium, of which mainly the following are to be named:

a strong NMR activity (relaxivity), so that the contrast medium, in as low concentrations as possible, lowers the relaxation times of the protons in the tissue fluid and other nuclei such as P, F and Na in vivo and thus makes possible the localization of tumors by increasing the signal intensity of the image obtained with the aid of nuclear magnetic tomography; as selective as possible a concentration and/or retention of the contrast medium at the target organ or cancerous tissue; sufficient water solubility; low toxicity; good tolerability; good chemical and biochemical stability.

Here, relevant for the image production are above all both the first-mentioned points. Since the relaxations times among the tissues differ at most only by a factor of 2-3 (T. E. Budinger and P. C. Lauterbur, Sciences 226, pp 288-298, 1984;), J. M. S. Hutchinson and F. W. Smith in Nuclear Magnetic Resonance Imaging Edit. C. L. Partain et al., pp 231-249, Saunders, N.Y. 1983) and the complexes and complex salts of the patents mentioned generally are flawed by the drawback that they distribute themselves only relatively unspecifically in the extracellular space and thus are not always suitable for a recognition of pathologically changed tissues, there exists a need above all for selectively bonding, tumor-specific compounds that can be used in diagnosis.

Now it has been known for a few years that porphyrin derivatives concentrate selectively in human and animal tumors (D. Kessel and T.-H. Chou, Cancer Res. 43, pp 1994-1999, 1983, P. Hambright, Bioinorg. Chem. 5, pp. 87-92, 1975; R. Lipson et al., Cancer 20, pp. 2250-2267, 1957, D. Sanderson et al., Cancer 30, pp 1368-1372, 1972). The first attempts to use this class of compounds also as diagnostic agents have also been described (J. Winkelmann et al., Cancer Research 27, pp 2060-2064, 1967; European patent application publication number 133603; N. J. Patronas et al., Cancer Treatment Reports 70, pp 391-395, 1986). With these compounds (tetrakis(4-sulfonatophenyl)- and tetrakis(4-carboxylatophenyl)-porphyrin), only the manganese(III) ion has proven suitable as a paramagnetic metal.

But the compounds previously described are far from satisfactorily fulfilling the criteria mentioned above; particular attention is still to be paid to their insufficient concentration in the target organs. An improvement of this property at the same time should help reduce the existing problems with toxicity and tolerability of the previously known compounds.

Therefore there continues to be a need, for many purposes, for complex compounds that are stable, easily soluble but also better tolerated, selectively bonding, easily accessible, have available a wider range of chemical variations of substituents (which, e.g., make possible the incorporation of metals other than manganese or several, also different, metals and thus simultaneously lead to a control of the properties and uses of the compounds) and that are suited for diagnosis and/or also therapy of tumors.

SUMMARY OF THE INVENTION

Thus, this invention makes these compounds and pharmaceutical agents available, and provides a process for their production.

It was found that complex compounds, consisting of a mesotetraphenylporphyrin ligand, optionally at least one ion of an element with atomic numbers 13, 21-32, 37-39, 42-44, 49, 50 or 57-83 as well as optionally cations of inorganic and/or organic bases, amino acids or amino acid amides, are surprisingly outstandingly suited for the production of NMR, X-ray, photo- and radio diagnostic agents as well as for phototherapeutic and radio therapeutic agents.

Preferred pharmaceutical agents, according to the invention exhibit, as porphyrin ligands, compounds of general formula I

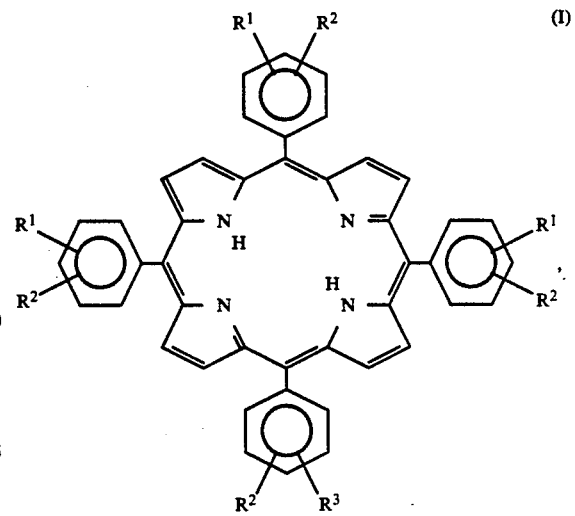

in which

R¹ means a CO-A, SO₂-A, OR⁵, R⁵, W, or NH-W radical with A in the meaning of an OH, OR⁴, NR⁵R⁶ or (NH)$_x$—[Q—(NH)$_y$]$_w$—W group, in which R⁴ is a C₁-C₆-alkyl or benzyl radical, R⁵ and R⁶ mean, independent of one another, hydrogen, a straight-chain or branched-chain or cyclic, saturated or unsaturated aliphatic hydrocarbon radical with up to 16 C-atoms, optionally substituted by one or more hydroxy or lower alkoxy groups, or R⁵, when R⁶ is hydrogen atom, can be an aryl or aralkyl group substituted optionally by one or more di-C₁-C₆ alkylamino groups or by one or more C₁-C₆ alkoxy groups, or R⁵ and R⁶, together with the nitrogen atom, mean a saturated or unsaturated 5- or 6-membered ring that optionally contains another nitrogen, oxygen, or sulfur atom or a carbonyl group and that is optionally substituted by one or more C₁-C₆ alkyl, or C₁-C₅ hydroxyalkyl radical(s), an optionally hydroxylated or C₁-C₆-alkoxylated C₂-C₆ acyl radical, hydroxy, carbamoyl, carbamoyl-substituted C₁-C₆ alkyl, a carbamoyl radical substituted at the carbamoyl-nitrogen by one or two C₁-C₆ alkyl radical(s), which can also form a ring optionally containing an oxygen atom, or a C₁-C₆ acylamino or C₁-C₆ alkylamino radical(s), x and y mean the numerals 0, 1 or 2, w means the numerals 0 or 1, Q means a C₁-C₂₀ alkylene group, W means a hydrogen atom or the grouping V-K, and V means a straight-chain, branched, saturated or unsaturated C₀-C₂₀ hydrocarbylene group optionally containing imino, polyethyleneoxy, phenylene, phenyleneoxy, phenyleneimino, amino, hydrazido, ester group(s), oxygen, sulfur and/or nitrogen atom(s) and optionally substituted by hydroxy, mercapto, imino, epoxy, oxo, thioxo and/or amino group(s), K means a hydrogen atom or a complexing agent of general formula IA, IB, IC or ID

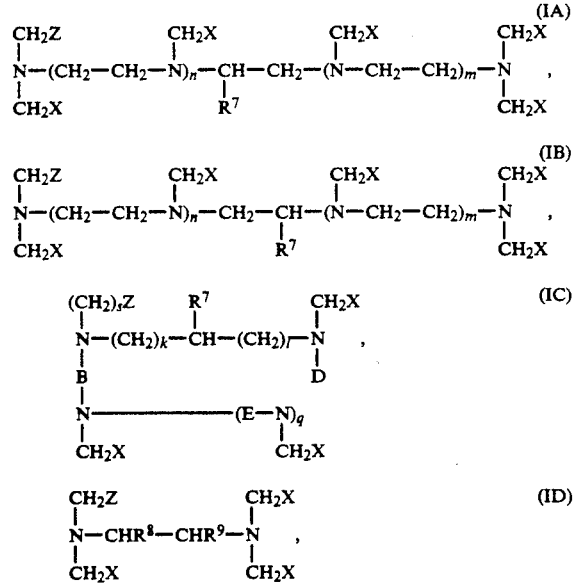

and n and m each stand for the numerals 0, 1, 2, 3, or 4, and n and m together result in no more than 4, k stands for the numerals 1, 2, 3, 4, or 5, l for the numerals 0, 1, 2, 3, 4, or 5, q for the numerals 0, 1, or 2, s for the numerals 0 or 1, X for —COOH, B, D and E, which are the same or different, each stand for the group $$-(CH_2)_u-\underset{\underset{R^{10}}{|}}{(CH)}_v-(CH_2)_l-$$

with

R¹⁰ in the meaning of hydrogen or a straight-chain, branched, saturated or unsaturated C₁-C₂₀ hydrocarbyl group optionally containing oxygen and/or nitrogen atom(s) and optionally substituted by hydroxy and/or amino group(s), u in the meaning of numerals 0, 1, 2, 3, 4 or 5, v in the meaning of the numerals 0 or 1, and B, D and E each contain at least 2 and at most 5 carbon atoms.

Z stands for the group $$\underset{\overset{\|}{-C-}}{\overset{O}{}}$$

or the radical X,

R⁷ for a direct bond or a hydrogen atom,

R⁸ and R⁹ together stand for a dimethylene- or trimethylenemethine group optionally substituted by 1-2 hydroxy or 1-3 C₁-C₄ alkyl groups, provided that Z stands for the group $$\underset{\overset{\|}{-C-}}{\overset{O}{}}$$

only when R⁷ simultaneously means a hydrogen atom and that Z stands for the radical X only when R⁷ simultaneously means a direct bond and s the numeral 1, R² stands for a hydrogen, fluorine, chlorine, bromine, iodine atom, or an R¹, R⁴ or OR⁴ group, R³ stands for one of the substituents indicated for R¹, with the exception of manganese(III) complexes of tetrakis(4-sulfonatophenyl)- and tetrakis(4-carboxylatophenyl) porphyrins and provided that, if desired, a portion of the COOH groups is present as ester and/or amide groups.

The invention further relates to complex compounds of general formula I, in which the substituents have the meanings indicated above and optionally at least one ion of an element with atomic numbers 13, 21-32, 37-39, 42-44, 49, 50 or 57-83 as well as optionally cations of inorganic and/or organic bases, amino acids or amino acid amides, with the exception of manganese(III) complexes of the tetrakis(4-sulfonatophenyl)- and tetrakis(4-carboxylatophenyl)-porphyrins as well as tetrakis(4-carbomethoxyphenyl)-, tetrakis(4-carboethoxyphenyl)-, tetrakis(3-carboxyphenyl)-, tetrakis(4-tetrakis(4-dimethylaminophenyl)-, tetrakis(4-diethylaminophenyl)-porphyrins.

In the metal complexes of general formula I, the ion of an element of atomic numbers 13, 21-32, 37-39, 42-44, 49, 50 or 57-83 is chelated by the porphyrin ring system, complexing agent K, or both. However, preferably, the ion is not chelated by the porphyrin ring. Alternatively, in the case of Mn, the porphyrin ring may desirably chelate the Mn ion.

In the compounds of general formula I, with or without at least one ion of an element with atomic numbers 13, 21–32, 37–39, 42–44, 49, 50 or 57–83, at least one of the $R^1$, $R^2$ and $R^3$ groups is other than H. In other words, preferably at least one of the phenyl groups of the mesotetraphenylporphyrin structure is substituted. Also, at least one of the $R^1$, $R^2$ and $R^3$ groups is preferably —CO—A; —SO$_2$—A; W, wherein W is other than H; or —NH—W, wherein W is H or —V—K. Moreover, preferably at least one of the $R^1$, $R^2$ and $R^3$ groups is not —SO$_3$H. Furthermore, preferably at least one of the $R^1$, $R^2$ and $R^3$ groups is neither a —SO$_3$H or —COOH group.

If the mesotetraphenylporphyrin ligand is a tetrakis(-sulfonatophenyl)-porphyrin, the porphyrin ring preferably does not chelate one of the following ions: Mn, Fe, Cr, Cu or Gd.

More specifically, with regard to complexes of general formula I wherein at least one ion of an element of atomic numbers 21–29, 42, 44 or 57–83 is chelated by the porphyrin ring system, complexing agent K, or both. It is preferred that the following complexes are excluded:

Mn(III) complex of tetrakis(4-sulfonatophenyl)-porphyrin;
Mn(III) complex of tetrakis(4-carboxylatophenyl)-porphyrin;
Fe(III) complex of tetrakis(phenylsulfonato)-porphyrin
Cu(II) complex of tetrakis(phenylsulfonato)-porphyrin;
Cr complexes of tetrakis(phenylsulfonato)-porphyrin;
Gd(III) complex of tetrakis(phenylsulfonato)-porphyrin;
Pt complexes of tetrakis(phenylsulfonato)-porphyrin; and
Ti complex of m-methyl-p-methoxyphenyl-porphyrin.

The synthesis described in J. Heterocyclic Chem. 3,495 (1966) of the free-metal porphyrins just described was performed for planned experiments in various biochemical and biological systems (e.g., bonding to proteins and nucleic acids, tissue distribution).

The complex compounds according to the invention include a total of four groups of compounds: a) compounds that contain no metal ion; b) compounds that contain one metal ion in the porphyrin ligand; c) compounds that contain at least one metal ion in the complexing agent radical K; and d) compounds that contain metal ions bonded in the porphyrin ligand as well as in the complexing agent radical K, and the metal ions can be different.

For the use of the agents according to the invention in photodiagnosis and phototherapy, preferably complex compounds that contain no metal ion are used.

If the agents according to the invention are intended for use in NMR diagnosis, paramagnetic metal ions must be present in the complex. These are in particular the divalent and trivalent ions of elements with atomic numbers 21–29, 42, 44 and 57–70. Suitable ions are, for example, the chromium(III), manganese(II), manganese(III), iron(II), cobalt(II), nickel(II), copper(II), praseodymium(III), neodymium(III), samarium(III) and ytterbium(III) ion. Because of their high magnetic moment, especially preferred are gadolinium(III), terbium(III), dysprosium(III), holmium(III), erbium(III) and iron(III) ions.

For use of the agents according to the invention in nuclear medicine, the metal ions must be radioactive. Suitable, for example, are radioisotopes of the elements copper, cobalt, gallium, germanium, yttrium, strontium, technetium, indium, ytterbium, gadolinium, samarium, thallium and iridium.

It is also possible that the radioactive isotope be complexed by the porphyrin ligand ((case b), see above), or the complexing agent radical K (case c) or that it be chelated by the complexing agent radical K while, simultaneously, the porphyrin ligand contains another metal ion, for example manganese(III) (case d). If the agents according to the invention are intended for use in X-ray diagnosis, then at least one metal ion in the complex must be derived from an element of a higher atomic number, to achieve sufficient absorption of the X-rays. It was found that for this purpose diagnostic agents that contain a physiologically tolerated complex salt with central ions of elements with atomic numbers among 21–29, 42, 44, 57–83 are suitable; these are, for example, the lanthanum(III) ion and the ions of the lanthanide series mentioned above.

An essential advantage of the metal complexes according to the invention containing the complexing agent radical K is that with them, the diagnostic or therapeutic effect caused by the metal ion can be intensified by incorporating another metal ion or that, by incorporating another metal ion different from the first one, in particular the physical properties can be improved by an intensification of a the magnetic effects and/or the X-ray absorption of the complex compounds.

Surprising here is that the essential properties such as, for example, especially the high selectivity and concentration of the complexes, that determine the effectiveness of these pharmaceutical agents are retained or improved.

With the aid of the complex compounds according to the invention, surprisingly not only tumor tissues and individual organs such as, for example, liver and kidneys, but also blood vessels can be visualized without using special pulse-sequences in vivo, and thus they can be used, among other things, as perfusion agents.

As an example for the ions bound in the porphyrin skeleton, there can be named the metals aluminum, manganese, iron, cobalt, nickel, copper, zinc, gallium, technetium, indium, tin, samarium, eruopium, gadolinium and thallium. Preferred are the metals aluminum, iron, cobalt, nickel, copper, zinc, gallium, technetium, indium, tin and especially manganese.

As alkyl substituent $R^4$, hydrocarbons with –6, preferably 1–4 C atoms are suitable, such as methyl, ethyl, propyl, isopropyl, n, sec. or tert.-butyl, isobutyl, pentyl and hexyl radicals.

As hydrocarbyl substituents $R^5$ and $R^6$, saturated, unsaturated, straight chain or branched chain or cyclic hydrocarbons with up to 16 C atoms are suitable, preferably saturated hydrocarbons with 1 to 10 C atoms, in particular saturated hydrocarbons atoms with 1 to 7 C atoms, that are optionally substituted by 1 to 5 hydroxy or lower alkoxy groups.

Lower alkoxy groups should in each case comprise 1 to 4 carbon atoms and in particular methoxy and ethoxy groups.

As optionally substituted alkyl groups, there can be named, for example, the groups methyl, ethyl, 2-hydroxyethyl, 2-hydroxy-1-(hydroxymethyl)-ethyl, 1-(hydroxymethyl)-ethyl, propyl, isopropyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2-, 3- and 4-hydroxy-2-methylbutyl, 2 and 3-hydroxyisobutyl, 2, 3, 4-trihydroxybutyl, 1,2,4- trihydroxybutyl, pentyl, cyclopentyl, cyclohexyl, 2,3,4,5,6-pentahydroxyhexyl and 2-methoxyethyl.

If $R^6$ stands for a hydrogen atom, $R^5$ can also mean a $C_6$-$C_{10}$ aryl or $C_6$-$C_{10}$-aryl-$C_1$-$C_6$ alkyl group, for example a phenyl or benzyl group, optionally substituted by one or more (up to three) di-$C_1$ to $C_6$ alkylamino groups or by one or more (up to three) C-$C_6$ alkoxy groups.

The heterocyclic 5- or 6-membered ring formed by $R^5$ and $R^6$ with amide nitrogen included can be saturated, unsaturated and/or substituted and optionally contain a nitrogen, oxygen or sulfur atom or a carbonyl group.

The heterocyclic moiety can be substituted by a hydroxy, a $C_1$-$C_6$ alkyl group, for example methyl, ethyl, propyl, isopropyl, butyl, a $C_1$-$C_5$ hydroxyalkyl group, for example, hydroxymethyl, hydroxyethyl, or by a $C_2$-$C_6$ acyl (e.g., alkanoyl) group, for example, acetyl, propionyl, that can optionally be substituted by a hydroxy or a $C_1$-$C_6$ alkoxy group, for example methoxy, ethoxy.

As another substituent there can be named the carbamoyl group that is bonded separately to the heterocyclic compound directly or by a $C_1$-$C_6$ alkylene group, for example, methylene, ethylene, propylene and is optionally substituted on the nitrogen by one or two $C_1$-$C_6$ alkyl radical(s), for example methyl, ethyl propyl, isopropyl, which optionally form a ring such as, for example, a pyrrolidine or piperidine ring. The carbamoyl nitrogen can also be an element of a morpholine ring.

As another possible substituent on the heterocyclic compounds, there is named an optionally $C_1$-$C_6$ alkylated or a $C_1$-$C_6$ acylated (e.g., by alkanoyl) primary or secondary amino group, such as for example the methyl, ethyl, acetyl, propionyl amino groups.

If the heterocyclic compound is substituted, the total number of substituents is 1 to 3.

As suitable heterocyclic compounds, there can be named as examples, the pyrrolidinyl, piperidyl, pyrazolidinyl, pyrrolinyl, pyrazolinyl, piperazinyl, morpholinyl, imadazolidinyl, oxazolidinyl and thiazolidinyl ring.

The alkylene group standing for V.or the alkyl group standing for $R^{10}$ can be straight-chain, branched, cyclic, aliphatic, aromatic or arylaliphatic, exhibiting up to 20 carbon atoms and optionally contain —NH—, —O—, —S—, —N—, —CO—O—, —O—CO—, (O—$CH_2C$-$H_2$—)poly, —NH—CO—, —CO—NH—, —NH—NH—, —$C_6H_4$—NH—, —$C_6H_4$—O—, —$C_6H_4$— groups. Preferred are the straight chain mono to decamethylene groups as well as $C_1$-$C_4$ alkylenephenyl groups.

The following alkylene groups are mentioned as examples for clarification: —$(CH_2)_2$NH—; —$CH_2$—O—$C_6H_4$—$CH_2$—; —$CH_2$—CH(OH)—$CH_2$—O—$C_6H_4$—$CH_2$—; —C(=NH)—O—$C_6H_4$—$CH_2$—; —$(CH_2)_4$—NH—CO—$CH_2$—O—$C_6H_4$—$CH_2$—; —$(CH_2)_4$—NH—$CH_2$—CH(OH)—$CH_2$—O—$C_6H_4$—$CH_2$—; —$(CH_2)_3$—O—$C_6H_4$—$CH_2$—; —$CH_2$—CO—NH—$(CH_2)_3$—O—$CH_2$—; —$CH_2$—CO—NH—NH—; —$CH_2$—CO—NH—$(CH_2)_2$—; —$CH_2$—CO—NH($CH_2$)$_{10}$—; —$CH_2$—CO—NH—$(CH_2)_2$—S—; —$(CH_2)_4$—NH—CO—$(CH_2)_8$—; —$CH_2$—CO—NH—$(CH_2)_3$—NH—; —$(CH_2)_3$—NH—; —$(CH_2)$—NH—C(=S)—NH—$C_6H_4$—$CH_2$—; —$(CH_2)_2$—NH—CO—CH—$CH_2$—(OCH$_2$CH$_2$)$_{43}$—OCH$_2$—.

See also, e.g., U.S. application Ser. No. 07/317,218.

As examples for the complexing agent radical K, there can be named those of ethylene diamine tetraacetic acid, diethylene triaminopentaacetic acid, trans-1,2-cyclohexanediamine tetraacetic acid, 1,4,7,10-tetraazacyclododecane tetraacetic acid, 1,4,7-triazacyclononane triacetic acid, 1,4,8,11-tetraazatetradecane tetraacetic acid and 1,5,9-triazacyclododecane triacetic acid, which are bonded by (in each case contained in K) one carbon atom or one carbonyl group to the porphyrin derivatives in each case. If desired, a part of the carboxylic acids can be present as an ester and/or amide.

The remaining acidic hydrogen atoms, i.e., those that have not been substituted by the central ion, can optionally be replaced completely or partially by cations of inorganic and/or organic bases or amino acids. The suitable acid groups can also be completely or partially converted into esters or amides.

Suitable inorganic cations are, for example, the lithium ion, the potassium ion, the calcium ion and especially the sodium ion. Suitable cations of organic bases are, among other, those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine and of ornithine as well as the amides of any other acidic or neutral amino acids.

Suitable esters are preferably those with one of the radicals indicated for $R^4$; for example the methyl, ethyl and tertiary butyl radicals can be named as examples.

If the carboxylic acid groups are present at least partially as amides, then those with the radicals indicated for $R^5$ and $R^6$ are suitable. Preferred are tertiary amides with saturated, unsaturated, straight chain or branched chain or cyclic hydrocarbon radicals with up to 5C atoms, which optionally are substituted by 1 to 3 hydroxy or $C_1$-$C_4$ alkoxy groups. There are, for example, the groups methyl, ethyl, 2-hydroxyethyl, 2-hydroxy-1-(hydroxymethyl)-ethyl, 1-(hydroxymethyl)-ethyl, propyl, isopropenyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2-, 3-, and 4-hydroxy-2-methylbutyl, 2 and 3-hydroxyisobutyl, 2,3,4-trihydroxybutyl, 1,2,4-trihydroxybutyl, pentyl, cyclopentyl, and 2-methoxyethyl.

Mentioned as preferred heterocyclic amide radicals are the rings pyrrolidinyl, piperidyl, pyrazolidinyl, pyrrolinyl, pyrazolinyl, piperazinyl, morpholinyl, imidazolidinyl, oxazolidinyl, thiazolidinyl.

The production of the mesotetraphenylporphyrin complex compounds according to the invention takes place in that conversion is performed into porphyrins of general formula II

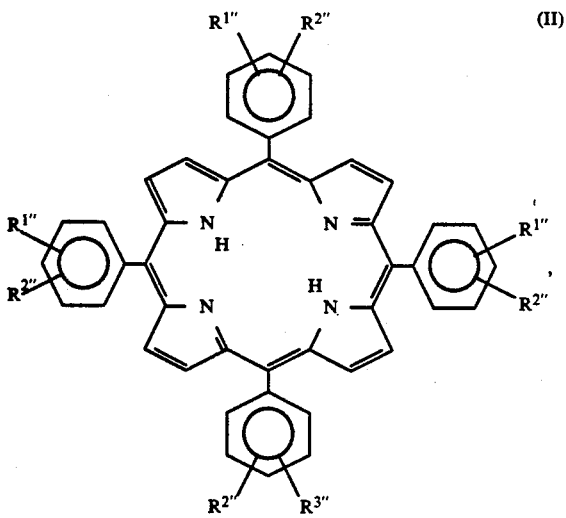

(II)

in which

R$^{1''}$ stands for R$^1$ or a substituent that can be converted into R$^1$,

R$^{2''}$ stands for a hydrogen, fluorine, chlorine, bromine, iodine atom, R$^{1''}$, R$^4$ or OR$^4$ R$^{3''}$ stands for one of the substituents indicated for R$^{1''}$ and R$^{1'}$, R$^{2'}$ and R$^{3'}$ have the meaning indicated for R$^1$, R$^2$ and R$^3$, but the substituent W stands for a hydrogen atom, optionally, in a way known in the art, into porphyrins of general formula II', in which R$^{1''}$ stands for R$^{1'}$, R$^{2''}$ for R$^{2'}$, and R$^{3''}$ for R$^{3'}$ and then, if desired, a) the pyrrolic NH's are substituted by the desired metal atom, optionally present protective groups are removed and then, if desired, the V-K radical is introduced and then reaction is performed with at least one metal oxide or metal salt of an element with atomic numbers 21-32, 37-39, 42-44, 49, 50 or 57-83 or b) substituent V-K is introduced, reacted with at least one metal oxide or metal salt of an element with atomic number 21-32, 37-39, 42-44, 49, 50 or 57-83 and then, if desired, the pyrrolic NH's are substituted by a metal atom or c) substituent V-K is introduced, the pyrrolic NH's are substituted by a metal atom and then reacted with at least one metal oxide or metal salt of an element with atomic numbers 21-32, 37-39, 42-44, 49, 50 or 57-83 and optionally, the acidic hydrogen atoms still present in the complex compounds obtained according to a), b) or c) are substituted by cations of inorganic and/or organic bases, amino acids or amino acid amides or the corresponding acids groups are completely or partially converted onto esters and/or amides.

Porphyrin educts (starting materials) are available, e.g., mesotetra(4-methoxyphenyl)-porphyrin from Aldrich Chemie GmbH, Steinheim, see example 17 are producible by methods known from the literature or analogous to those known in the literature [e.g., mesotetra(4 sulfonatophenyl)-porphyrin: J. Winkelman et al., Cancer Res. 27, 2060, 1967; mesotetra(4-aminophenyl)-porphyrin: A. S. Semeikin et al., C.A. 105, 1986, 13361h; mesotetra(4-carboxyphenyl)porphyrin: J. Lindsey et al., J. Org. Chem. 52, 827, 1987; mesotetra(3-trifluoromethylphenyl)-porphyrin: ring synthetically similar to Y. San et al., J. Heterocyclic Chem. 23, 561, 1986, Falk, Porphyrins and Metalloporphyrins, Elsevier 1975, D. Dolphin, The Porphyrins, Academic Press, 1978; K. M. Smith, Porphyrins and Metalloporphyrins, Elsevier, Amsterdam, 1975).

They are converted in a way known in the art into the porphyrin derivatives of general formula II', e.g., by sulfonation (R. D. Macfarlene et al., J. Heterocyclic Chem. 23, 1565, 1986; Houben-Weyl, Methods of Organic Chemistry [Methoden der Organischen Chemie], volume IX, 1955, page 450, Georg Thieme Verlag Stuttgart), by hydrolysis of CF$_3$ substituents into carboxyl groups (Houben-Weyl, Methods of Organic Chemistry, Volume V/3, 1962, p 473, Georg Thieme Verlag, Stuttgart), by nitration and subsequent reduction into an amino group (Y. Sun et al., J. Heterocyclic Chem., 23, 561, 1986, Houben-Weyl, Methods of Organic Chemistry, volume X/1, 1971, p. 478, Georg Thieme Verlag, Stuttgart), by esterification (L. R. Milgram, J. Chem. Soc. Perkin Trans I 1984, 1483). etc.

The production of amides, i.e., of compounds of general formula I, in which R$^1$ stands for CONR$^5$R$^6$, is performed by the reaction of activated porphyrin acid derivatives (e.g., mixed anhydride, acid chloride) with primary or secondary amines of the general formula

in which R$^5$ and R$^6$ have the meaning indicated above.

As suitable amines, there can be named, for example, dimethylamine, diethylamine, di-n-propylamine, diisopropylamine, di-n-butylamine, diisobutylamine, di-sec.-butylamine, N-methylene propylamine, dioctylamine, dicyclohexylamine, N-ethylcyclohexylamine, diisopropenylamine, benzylamine, aniline, 4-methoxyaniline, 4-dimethylaminoaniline, 3,5-dimethoxyaniline, morpholine, pyrrolidine, piperidine, N-methylpiperazine, N-ethylpiperazine, N-(2-hydroxyethyl)-piperazine, N-hydroxymethyl)piperazine, piperazinoacetic acid isopropylamide, N-piperazinomethylcarbonylmorpholine, N-(piperazinomethylcarbonyl)-pyrrolidine, 2-(2-hydroxymethyl)-piperidine, 4-(2-hydroxyethyl)-piperidine, 2-hydroxymethylpiperidine, 4-hydroxymethylpiperidine, 2-hydroxymethyl-pyrrolidine, 3-hydroxypiperidine, 4-hydroxypiperidine, 3-hydroxypyrrolidine, 4-piperidone, 3-pyrroline, piperidine-3-carboxylic acid amide, piperidine-4-carboxylic acid amide, piperidine-3-carboxylic acid diethylamide, piperidine-4-carboxylic acid dimethylamide, 2,6-dimethylpiperidine, 2,6-dimethylmorpholine, N-acetylpiperazine, N-(2-hydroxypropionyl)-piperazine, N-(3-hydroxypropionyl)piperazine, N(methoxyacetyl)-piperazine, 4-(N-acetyl-N-methylamino)-piperidine, piperidine-4-carboxylic acid-(3)oxapentamethylene)-amide, piperidine-3-carboxylic acid-(3-oxapentamethylene)-amide, N-(N',N'-dimethylcarbamoyl)-piperazine, pyrazoline, imidazoline, oxazolidine, thiazolidine, 2,3-dihydroxypropylamine, N-methyl-2,3-dihydroxypropylamine, 2-hydroxy-1-(hydroxymethyl)-ethylamine, N,N-bis-(2-hydroxyethyl) amine, N-methyl-2,3,4,5,6-pentahydroxyhexylamine, 6-amino-2,2-dimethyl-1,3-dioxepin-5-ol, 2-hydroxyethylamine, 2-amino-1,3-propanediol, diethanolamine, ethanolamine.

The polyhydroxyalkylamines can advantageously also be added in protected form to the reaction, for example, as O-acyl derivatives or as ketals. This applies especially when these derivatives can be produced more conveniently and less expensively than the polyhydroxyalkylamines themselves. A typical example is 2-amino-1-(2,2-dimethyl-1,3-dioxolan-4-yl)-ethanol, the acetonide of 1-amino-2,3,4-trihydroxybutane, produced according to DE-OS 31 50 917.

The disadvantageous removal of the protective groups is not a problem and can, for example, be performed by treatment with an acidic ion exchanger in an aqueous-ethanolic solution.

To produce aminoalkylene substituted porphyrin amide derivatives (that can act as educts for the porphyrin complexes containing the substituent K), the activated prophyrin acid derivatives mentioned above can be reacted with terminal alkylenediamines, one amino group of which is protected, for example, in the form of the carbobenzoxy radical. The removal of the protective group is then performed according to methods known from the literature, for example, by treatment with trifluoroacetic acid.

To introduce the complexing agent radical K, the compounds thus obtained in a way known in the art can be reacted with isothiocyanatobenzyl-substituted complexing agents (O. Gansow et al., Inorg. Chem 25, 2772, 1986), amidated, hydrazinated (Houben-Weyl, Methods of Organic Chemistry, volume VIII/3, Georg Thieme Verlag, Stuttgart (1952), 654 and 676), acylated (J. March, Advanced Organic Chemistry, McGraw-Hill, 2nd ed., (1977) 377-382) and/or alkylated (Houben-Weyl, Methods of Organic Chemistry, Volume VI/3, Georg Thieme Verlag, Stuttgart (1965), 187).

As a substrate for the introduction of units V-K, compounds of general formulas I'A, I'B, I'C, I'D, I"AB, I"C and I"D can be used:

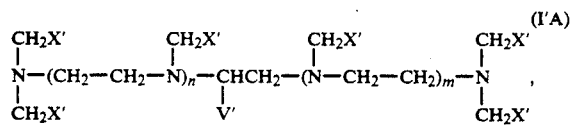
(I'A)

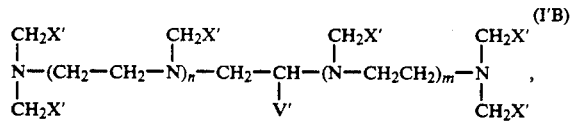
(I'B)

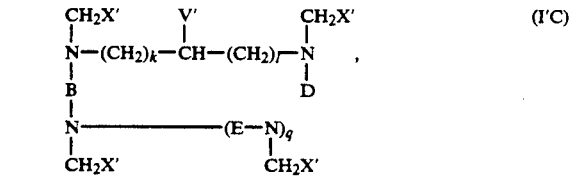
(I'C)

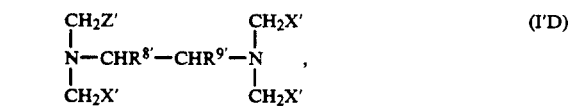
(I'D)

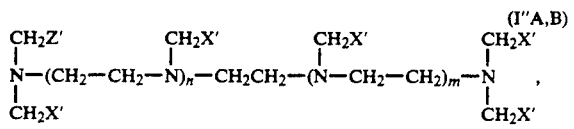
(I"A,B)

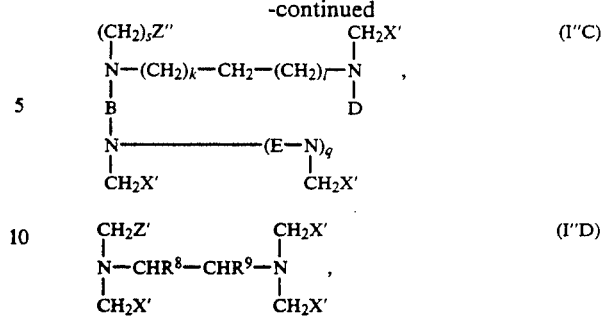

in which V' stands for a substituent to be converted into V, $R^{8'}$ and $R^{9'}$ stand for $R^8$ and $R^9$, which contain substituent V', X' stands for COOY with Y in the meaning of hydrogen or an acid protective group, Z' stands for an activated carbonyl group and Z" stands for Z' or, in the case of s=0, for hydrogen.

In the last-mentioned case (I"C with s=O and Z"=H), the compounds of general formula I"C are reacted with activated porphyrin acid derivatives.

As an example for a activated carbonyl group, there can be named anhydride (this can also be formed with the neighboring acid group of the same molecule), p-nitrophenyl acid ester and acid chloride.

As acid protective groups Y, lower alkyl, aryl, and aralkyl groups, for example, methyl, ethyl, propyl, butyl, phenyl, benzyl, diphenylmethyl, triphenylmethyl, bis(p-nitrophenyl)-methyl groups are suitable, as well as trialkylsilyl groups.

The cleavage of protective groups Y is performed according to processes known to one skilled in the art, for example, by hydrolysis, alkaline saponification of the esters with alkalis in aqueous-alcoholic solution at temperatures of 0° C. to 50° C., or in the case of tert.-butyl esters, with the aid of trifluoroacetic acid.

The alkylation or acylation performed for the introduction of the complexing agent units is performed with reagents that contain the desired K-V substituent (bonded to a leaving group) or from which the desired substituent, optionally after modification by secondary reaction(s), is generated by the reaction. As examples for the ones mentioned first there can be named halides, mesylates, tolsylates and anhydrides. To the second group there belong, for example, oxiranes, thiiranes, aziranes, alpha, beta unsaturated carbonyl compounds or their vinylogs, aldehydes, ketones, isothiocyanates and isocyanates.

As examples for secondary reactions, there are named hydrogenations, esterifications, oxidations, etherifications and alkylations, which are performed according to literature processes known to one skilled in the art.

Compounds I' needed as educts are known (e.g., European patent application publication number 0154788) or can be produced from suitable polyamines (and available functional groups are optionally protected) by alkylation with an ester of general formula III

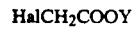 HalCH$_2$COOY (III), in which Hal stands for chlorine, bromine or iodine.

The reaction occurs in polar, aprotic solvents such as, for example, dimethylformamide, dimethylsulfoxide or hexamethylphosphoric acid triamide in the presence of an acid trap, such as for example tertiary amine (for example triethylamine, trimethylamine, N,N-dimethylaminopyridine, 1,5-diazabicyclo[4.3.0]nonene-5(DBN), 1,5-diazabicyclo[5.4.0]undecene-5(DNU), alkali or alkaline earth carbonate or hydrogen carbonate (for example, sodium, magnesium, calcium, barium, potassium carbonate and hydrogen carbonate) at temperatures between −10° C. and 120° C., preferably between 0° C. and 50° C.

The production of activated carbonyl derivatives I″ (e.g., mixed anhydride, N-hydroxysuccinimide esters, acylimidazoles, trimethylsilyl ester) is performed according to methods known from the literature [Houben-Weyl, Methods of Organic Chemistry, Georg Thieme Verlag, Stuttgart, Volume E 5(1985), 633; Org. React. 12, 157 (1962)] or is described in the experimental part.

The suitable polyamines needed as educts for the production of the polyamine poly acids of general formula I′A are produced in analogy to methods known from the literature (for example, Canad. Patent No. 1 178 951, Euro. I. Med. Chem.-Chim. Ther. 1985, 20 509 and 1986, 21, 333) in that the start is made from amino acids that are converted into optionally ethylene amine-substituted amides (for example, with N-(2-aminoethyl)-carbamic acid benzyl ester) and are then reduced (optionally after cleavage of the protective groups) to the desired amines (preferably with diborane or lithium aluminum hydride).

If it is desired to synthesize the polyamine educts for the compounds of general formula I′B, it is necessary, before the reduction, to substitute such an amide at the alpha amino group by reaction with, for example, ethyloxamate, in a polar solvent such as, for example, tetrahydrofuran, dimethylsulfoxide or dimethoxyethane at a temperature between 50° C. and 250° C., preferably 70° C. to 150° C. (optionally in a pressure vessel), so that a 3-aza-2-oxo-glutaric acid diamide derivative is obtained as an intermediate product.

The production of the cyclic polyamides needed as educts for I′C or I″C is performed by cyclization of two reactants, one of which (in the case of synthesis of I′C) is V′-substituted.

The cyclization is performed according to methods known from the literature, for example, Org. Synth. 58,86 (1978), Macrocyclic Polyether Syntheses, Springer Verlag, Berlin, Heidelberg, New York, 1982, Coord. Chem. Rev. 3,3 (1968), Ann. Chem. 1976, 916: one of the two reactants carries, on the chain end, two leaving groups, the other carries two nitrogen atoms than nucleophilicly displace these leaving groups. As an example, there can be named the reaction of terminal dibromo, dimesyloxy, ditosyloxy or dialkoxycarbonylalkylene compounds containing optionally one or two nitrogen atom(s) with terminal diazaalkylene compounds containing optionally one or two additional nitrogen atom(s) in the alkylene chain, of which (in the case of synthesis of I′C) one of the two reactants is V′-substituted.

The nitrogen atoms are optionally protected, for example as tosylates, and are released before the following alkylation reaction according to processes known form the literature.

If diesters are added to the cyclization reaction, the diketo compounds thus obtained must be reduced according to processes known to one skilled in the art, for example with diborane.

As substituent V′ that can be converted into V, there are suited, among others, hydroxy and nitrobenzyl, hydroxy and carboxyalkyl and thioalkyl radicals with up to 20 carbon atoms. They are converted according to processes from the literature known to one skilled in the art (Chem. Pharm. Bull. 33,674, (1985), Compendium of Org. Synthesis Vol. 1-5, Wiley and Sons, Inc., Houben-Weyl, Methods of Organic Chemistry, Volume VIII, Georg Thieme Verlag, Stuttgart, J. Biochem. 92, 1413, 1982) into the desired substituents (for example, with the amino, hydrazine, hydrazinocarbonyl, epoxide, anhydride, halogen, halogenocarbonyl, mercapto, isothiocyanate group as functional group), and in the case of the nitrobenzyl radical, first a catalytic hydrogenation (for example, according to P. N. Rylander, Catalytic Hydrogenation over Platinum Metals, Academic Press 1967) into the aminobenzyl derivative must be performed.

Examples for the conversion of hydroxy or amino groups bonded to aromatic or aliphatic radicals are the conversions performed in anhydrous, aprotic solvents such as tetrahydrofuran, dimethoxyethane or dimethylsulfoxide in the presence of an acid trap such as, for example, sodium hydroxide, sodium hydride or alkali or alkaline earth carbonates such as, for example, sodium, magnesium, potassium, calcium carbonate at temperatures between 0° C. and the boiling point of the respective solvent, but preferably between 20° C. and 60° C., with a substrate of general formula IV

in which Nf stands for a nucleofuge such as, e.g., Cl, Br, I, $CH_3C_6H_4SO_3$ or $CF_3SO_3$, L stands for an aliphatic, aromatic, arylaliphatic, branched, straight-chain or cyclic hydrocarbon radical with up to 20 carbon atoms and Fu stands for the desired terminal functional group, optionally in protected form (DE-OS 34 17 413).

As examples for compounds of general formula IV there can be named $Br(CH_2)_2NH_2$, $Br(CH_2)_3OH$, $BrCH_2COOCH_3$, $BrCH_2CO_2{}^tBu$, $ClCH_2CONHNH_2$, $Br(CH_2)_4CO_2C_2H_5$, $BrCH_2COBr$, $ClCH_2COOC_2H_5$, $BrCH_2CONHNH_2$,

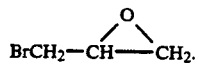

Conversions from carboxy groups can be performed, for example, according to the carbodiimide method (Fieser, Reagents for Organic Syntheses 10, 142), by a mixed anhydride [Org. Prep. Proc. Int. 7,215(1975)] or by an activated ester (Adv. Org. Chem. Part B, 472).

The production of the amines needed as starting substances for the cyclization is performed according to methods known from the literature.

Starting from an N-protected amino acid, a triamine is obtained by reaction with a partially protected diamine (for example according to the carbodiimide method), cleavage of the protective groups and diborane reduction.

The reaction of a diamine that can be obtained from amino acids (Eur. J. Med. Chem.-Chim. Ther. 21,333 (1986), with double the molar amount of an N-protected omega amino acid yields a tetramine after suitable working up.

In both cases, the number of carbon atoms between the N atoms can be determined by the type of diamines or amino acids used as the coupling partner.

The introduction of the desired metals (e.g., Mn, Fe, Co, Ni, Cu, Zn, Ga, In, Tc, Sn, Sm, Eu, Gd, Tl) into the porphyrin ligands is performed according to methods known from the literature (The Porphyrins, ed. D. Dolphin, Academic Press, New York, 1980, Vol. V, p 459) by warming with the appropriate metal salts, preferably the acetates, optionally with the addition of acid-buffering agents such a sodium acetate. As solvents, primarily polar solvents such as, for example, chloroform, acetic acid, methanol, ethanol, dimethylformamide, and water are suited.

The complexing is to be performed as much as possible with light exclusion, since a photochemical degradation of the porphyrins can occur.

Preferred metals are manganese, technetium, gallium and indium. If the complex compound according to the invention contains the radical K, then the introduction of the porphyrin metal can occur before or after connection of the complexing agent radical K as well as before or after chelation of the complexing agent with a metal. This makes possible an especially flexible procedure for the synthesis of the compounds according to the invention so that, for example, metals with a short half-life, for example $^{111}$In, be it in the porphyrin ligand or in the complexing agent, can be introduced first in the last synthesis step.

The chelation of the radical K can be performed as it has been disclosed in patent DE-OS 34 01 052, in that the metal oxide or a metal salt (for example the nitrate, acetate, carbonate, chloride or sulfate) of the element with atomic number 21-32, 37-39, 42-44, 49, 57-83 is dissolved or suspended in water and/or in a lower alcohol (such as methanol, ethanol or isopropanol) and is reacted with the solution or suspension of the equivalent amount of the complexing ligand and then, if desired, available acidic hydrogen atoms of the acid groups are substituted by cations of inorganic and/or organic bases or amino acids.

The neutralization is performed here with the aid of inorganic bases (for example hydroxides, carbonates or bicarbonates) of, for example, sodium, potassium, lithium, magnesium or calcium and/or of organic bases such as, among others, primary, secondary and tertiary amines, such as for example ethanolamine, morpholine, glucamine, N-methyl and N,N-dimethylglucamine, as well as of basic amino acids, such as for example lysine, arginine and ornithine or of amides of originally neutral or acidic amino acids.

To produce the neutral complex compounds, for example, there can be added to the acidic complex salts in aqueous solution or ion suspension an amount of the desired bases such that the neutral point is reached. The solution obtained can then be evaporated to dryness in a vacuum. Often it is advantageous to precipitate the neutral salts formed by adding solvents miscible with water such as, for example, lower alcohols (methanol, ethanol, isopropanol and others), lower ketones (acetone and others), polar ethers (tetrahydrofuran, dioxane, 1,2-dimethoxyethane and others) and thus to obtain crystallizates that are easy to isolate and purify. It has been proven to be especially advantageous to add the desired base already during the complexing of the reaction mixture and thus to skip one process step.

If the acidic complex compounds contain several free acidic groups, it is often suitable to produce neutral mixed salts that contain inorganic as well as organic cations as counterions.

This can occur, for example, in that the complexing ligand is reacted in aqueous suspension or solution with the oxide or salt of the element yielding the central ion and with half the amount of an organic base needed for neutralization, the complex salt formed is isolated, purified if desired and then mixed until complete neutralization with the necessary amount of inorganic base. The sequence of the base addition can also be reversed.

Another possibility of arriving at neutral complex compounds consists in converting the remaining acid groups in the complex completely or partially into, for example, esters or amides. This can occur by subsequent reaction on the finished complex (e.g., by exhaustive reaction of the free carboxy or phosphonic acid groups with dimethylsulfate) and by use of a suitably derived substrate for the introduction of complexing units K-V of general formula I'A, I'B, I'C, I'D, I''AB, I''C, I''D (e.g., N$^3$-(2,6-dioxomorpholinomethyl)-N$^6$-(ethoxycarbonylmethyl)-3,6-diazaoctanedioic acid).

In the case of use of complex compounds containing radioisotopes, their production can be performed according to the methods described in "Radiotracers for Medical Applications", Volume 1, CRC Press, Boca Raton, Fla.

The production of the pharmaceutical agents according to the invention also is performed in a way known in the art in that the complex compounds according to the invention—optionally with the addition of admixtures common in galenicals—are suspended or dissolved in an aqueous medium and then the suspension or solution is optionally sterilized. Suitable additives are, for example, physiologically harmless buffers (such as for example trimethamine), limited admixtures of complexing agents (such as for example diethylenetriaminepentaacetic acid) or, if necessary, electrolytes such as for example sodium chloride or, if necessary, antioxidants such as ascorbic acid.

If, for enteral administration or other purposes, suspensions or solutions of the agents according to the invention in water or in physiological salt solution are desired, they are mixed with one or more inactive ingredient(s) common in galenicals (for example, methylcellulose, lactose, mannitol) and/or surfactant(s) (for example, lecithins, Tween ®, Myrj ®) and/or aromatic substance(s) for taste adjustment (for example, essential oils).

In principle it is also possible to produce the pharmaceutical agents according to the invention also without isolation of the complex salts. In any case, special care must be taken to perform the chelation so that the salts and salt solutions according to the invention are practically without uncomplexed metal ions with a toxic effect.

This can be guaranteed, for example, with the aid of color indicators such as xylenol orange by control titration during the production process. The invention thus relates also to processes for the production of the complex compounds and their salts. As the last safety measure there remains a purification of the isolated complex salt.

The pharmaceutical agents according to the invention preferably contain 70 micromol/L to 70 mmole/L in the form of its complex salt and, as a rule, are dosed in amounts of 0.1 micromol to 1 mmole/kg of body weight. They are intended for enteral and parenteral administration.

The complex compounds according to the invention are used:

1. for NMR and X-ray diagnosis in the form of their complexes with the ions of elements with atomic numbers 21-29, 42, 44 and 57-83;

2. for radiodiagnosis and radiotherapy in the form of their complexes with radioisotopes of elements with atomic numbers 27, 29–32, 37–39, 43, 49, 62, 64, 70 and 77.

3. for photodiagnosis and phototherapy, preferably in the form of their metal-free porphyrins.

The agents according to the invention fulfill the numerous conditions for suitability as contrast agents for nuclear magnetic tomography. For this purpose they are outstandingly suited, after enteral or parenteral application, by increasing the signal intensity, to improve the ability of the image obtained with the aid of nuclear magnetic tomography to convey information. Further, they show the high efficacy that is necessary to burden the body with as small an amount as possible of foreign substances and the good tolerability that is necessary to maintain the noninvasive nature of the tests.

The good water solubility of the agents according to the invention makes it possible to produce highly concentrated solutions so that the volume load of the cardiovascular system can be kept within acceptable limits and the dilution by body fluids can be balanced. Further, the agents according to the invention exhibit not only a high stability in vitro, but also a surprisingly high stability in vivo, so that a release or an exchange of the ions — poisonous in and of themselves — not convalently bonded in the complexes occurs only extremely slowly within the time during which the new contrast agents are again completely excreted.

In general, the agents according to the invention are dosed for use as NMR diagnostic agents in amounts of 5 micromol to 100 micromol/kg of body weight, preferably 50 micromol to 100 micromol. Details of use are discussed, for example, in H. J. Weinmann et al., Am. J. of Roentgenology 142, 619 (1984).

Especially low dosages (below 1 mg/kg of body weight) of organ-specific NMR diagnostic agents can be used, for example, for detecting tumors and cardiac infarction.

Further, the complex compounds according to the invention can be used advantageously as susceptibility reagents and as shift reagents for in-vivo NMR spectroscopy.

The agents according to the invention, because of their favorable radioactive properties and the good stability of the complex compounds they contain, are also suited as radiodiagnostic agents. Details of their use and dosage are described, e.g., in "Radiotracers for Medical Applications," CRC Press, Boca Raton, Fla.

Another imaging method with radioisotopes is positron-emission tomography, which uses positron-emitting isotopes such as, e.g., $^{43}$Sc, $^{44}$Sc, $^{52}$Fe, $^{55}$Co, $^{68}$Ga and $^{81}$Rb (Heis, W. D. Phelps, M. E. Positron Emission Tomography of Brain, Springer Verlag Berlin, Heidelberg, New York, 1983).

The compounds according to the invention can also be used in radio-immunotherapy. This differs from the corresponding diagnostic agent only by the amount and type of radioactive isotope used. Here the object is the destruction of tumor cells by energy-rich, shortwave radiation with as limited as possible a range. The specificity of the complex according to the invention here is of decisive significance, since unspecifically localized complexes lead to the destruction of healthy tissue.

At the target site, the metal ion selected because of its cell-killing properties emits rays that lethally harm the cells. Suitable beta-emitting ions are, for example, $^{46}$Sc, $^{47}$Sc, $^{48}$Sc, $^{72}$Ga and $^{73}$Ga. Alpha-emitting ions exhibiting suitable short half-lives are, for example, $^{211}$Bi, $^{212}$Bi, $^{213}$Bi and $^{214}$Bi, and $^{212}$Bi is preferred. A suitable photon- and electron-emitting ion is $^{158}$Gd, which can be obtained from $^{157}$Gd by neutron capture.

With in-vivo administration of the therapeutic agents according to the invention, the latter can be administered together with a suitable vehicle such as, for example, serum or physiological common salt solution and together with another protein such as, for example, human serum albumin. The dosage here depends on the type of cellular disruption and the metal ion used.

The therapeutic agents according to the invention are administered parenterally, preferably intravenously.

Details of the use of radiotherapeutic agents are discussed, for example, in R. W. Kozak et al., TIBTEC, October 1986, 262.

The agents according to the invention are also suited as X-ray contrast agents, and it is especially to be emphasized that, also compared to previously common, iodine-containing contrast agents, they reveal pharmacokinetics that considerably promote diagnosis. Further, they are especially valuable further because of the favorable absorption properties in ranges of higher tube tensions for digital subtraction techniques.

Generally, the agents according to the invention are dosed for use as X-ray contrast agents similar to, for example, meglumine diatrizoate, in amounts of 100 micromol to 1mmole/kg of body weight, preferably 300 micromol to 800 micromol/kg of body weight.

Details of the use of X-ray contrast agents are discussed, for example, in Barke, X-Ray contrast agents, G. Thieme, Leipzig (1970) and P. Thurn, E. Buecheler, Introduction to X-Ray Diagnosis, G. Thieme, Stuttgart, New York, (1977).

The compounds according to the invention are also especially suited for photodiagnosis and phototherapy. This methodology was previously affected by the drawback that — caused by an unspecific bonding of porphyrin — damage to healthy tissue can easily result. The high incorporation rate of the compounds according to the invention make it possible to prevent or at least reduce the applied dose and thus the undesired phototoxic effect on healthy tissue. Preferably metal-free porphyrins are used here; they have the property, during exposure to light with about a 400 nm wavelength, of fluorescing and thus showing the location of the tumor. During exposure to light with a wavelength of about 630 nm, they release singlet oxygen that destroys the tumor cells.

Generally, the agents according to the invention are dosed for use as photodiagnostic agents or as phototherapeutic agents in amounts of 0.1 micromol to 5 micromol or 1 micromol to 20 micromol, preferably 0.5 micromol to 2.5 micromol or 2.5 micromol to 10 micromol/kg of body weight. They are administered parenterally, preferably intravenously.

Details of the use of porphyrins as photodiagnostic agents and as phototherapeutic agents are discussed, for example, in D. A. Cortese et al., Mayo Clin. Proc. 54:635–642, 1979; T. J. Dougherty, Cancer Res., 42:1188, 1982, T. J. Dougherty, Porphyrin Photosensitization, pp. 3–13, New York, Plenum Publishing Corp. 1982; T. J. Dougherty et al., Cancer REs. 38:2628–2635, 1978.

Overall, new complex compounds were successfully synthesized that yield new possibilities in diagnostic and therapeutic medicine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, cited above and below, and of corresponding German application P 38 09 671.4, are hereby incorporated by reference.

EXAMPLE 1

Manganese(III)<5,10,15,20-tetrakis{[4-carboxylic acid-(2,3,4-trihydroxybutyl)amide]-phenyl}-porphyrin>-acetate a) mesotetra(4-chlorocarbonylphenyl)-porphyrin To a suspension of 791 mg (1mmole) of mesotetra(4-carboxyphenyl)-porphyrin (J. Lindsey et al., J. Orig. Chem. 52, 827, 1987) in 10 ml of dry benzene there is added 10 ml (112 mmole) of oxalylchloride. Next, with moisture exclusion, it is heated for 3 hours to 80° C. Then it is evaporated in a vacuum to dryness and freed by the oil pump from the last remains of leaving portions. The title compound is obtained as a green powder.

b) 5,10,15,20-Tetrakis {4-carboxylic acid-[2-hydroxy-2-(2,2-dimethyl-1,3dioxolan-4-yl)-ethyl]amide}-phenyl>-porphyrin To the solution of 750 mg (4.65 mmole) of 2-amino-1-(2,2-dimethyl-1,3-dioxolan-4-yl)-ethanol and 1 ml (7.17 mmole) of triethylamine in 250 ml of absolute tetrahydrofuran, the acid chloride produced under a) is added in portions with stirring, cooling and exclusion of moisture. Thereafter it is stirred for another 3.5 hours at room temperature. The solvent is mostly drawn off in the vacuum, the residue is diluted with dichloromethane and the solution is washed with 1N sodium hydroxide solution and water. The organic solution is dried over sodium sulfate and evaporated to dryness in a vacuum. The residue is recrystallized from ethanol and dried in the vacuum at 80° C. Thus 770 mg (56.6% of theory) of the title compound is obtained with a melting point of 240-242° C.

| Analysis: | | | |
|---|---|---|---|
| Calculated: | C 66.95 | H 6.06 | N 8.22 |
| Found: | C 66.59 | H 6.28 | N 8.04 | c) Manganese(III)-Σ 5,10,15,20-tetrakis <-{4-carboxylic acid[2-hydroxy-2-(2,2-dimethyl-1,3-dioxolan-4-yl)-ethyl]-amide }-phenyl >-porphyrin Σ -acetate 164 mg (2 mmol) of anhydrous sodium acetate is suspended in 100 ml of dimethylformamide (DMF). It is heated to 100° C. and, with stirring, 682 mg (0.5 mmol) of the porphyrin produced under 1b) is added. The temperature is raised to 150° C. Now 490 mg (20 mmol) of manganese(II)-acetate tetrahydrate is added, which is accomplished by much foaming. The solution is refluxed gently, and the color changes from red to green. After 30 minutes, no starting material can be detected with thin film chromatography. After cooling, the solvent is drawn off in a vacuum. The residue is taken up in tetrahydrofuran/a little ethanol, filtered and again concentrated by evaporation. It is now taken up in plenty of dichloromethane, washed with distilled water, the organic solution is dried over sodium sulfate and is evaporated in a vacuum to dryness. The residue is dried in a vacuum at 70° C. 600 mg (81.1% of theory) of the title compound with a melting range around 245° C. is obtained this way.

| Analysis: | | | |
|---|---|---|---|
| Calculated: | C 63.49 | H 5.67 | N 7.59 | Mn 3.72 |
| Found: | C 63.22 | H 5.83 | N 7.73 | Mn 3.86 | d) Manganese(III)-<5,10,15,20-tetrakis-{[-4-carboxylic acid-(2,3,4-trihydroxybutyl)-amide]-phenyl }-porphyrin -acetate 600 mg (0.41 mmol) of the manganese complex produced under 1c) is dissolved in a mixture of 10 ml of distilled water and 5 ml of glacial acetic acid and heated for 30 minutes with darkening to 80° C. No more starting material shows in the thin film chromatogram after this time. The solution is evaporated in a vacuum to dryness, again taken up in water and lyophilized. The product is obtained as a dark green foam.

The manganese determination is performed by AAS.
Yield: 470 mg (87.2% of theory).

| Analysis: | | | | |
|---|---|---|---|---|
| Calculated: | C 60.27 | H 5.13 | N 8.52 | Mn 4.18 | O 21.90 |
| Found: | C 60.21 | H 5.20 | N 8.46 | Mn 4.15 |

EXAMPLE 2

Manganese(III)- {5,10,15,20-tetrakis <[4-carboxylic acid-(2,3-dihydroxy-1-hydroxymethylpropyl)-amide]-phenyl>-prophyrin}-acetate a) Mesotetra-(4-chlorocarbonylphenyl)-porphyrin 791 mg (1 mmol) of mesotetra-(4-carboxyphenyl)-porphyrin and 10 ml (112 mmol) of oxalylchloride are reacted as described under 1a) into acid chloride that is reacted without further purification into 2b.

b) 5,10,15,20-Tetrakis {[4-carboxylic acid-(5-hydroxy-2,2-dimethyl-1,3-dioxepan-6-yl)-amide]phenyl }-porphyrin A solution of 750 mg (4.65 mmol) of 6-amino-2,2-dimethyl-1,3-dioxepan-5-ol and 1 ml (7.17 mmol of triethylamine in 250 ml of absolute tetrahydrofuran is reacted as described under 1b) with the acid chloride produced under 2a). After crystallization from ethanol, 840 mg of the product is obtained. Melting point 218-220° C.

| Analysis: | | | |
|---|---|---|---|
| Calculated: | C 66.95 | H 6.06 | N 8.22 |
| Found: | C 66.67 | H 6.19 | N 8.09 | c) Manganese(III)- {5,10,15,20-tetrakis <[4-carboxylic acid-(5-hydroxy-2,2-dimethyl-1,3-dioxepan-6-yl)-amide]-phenyl >-porphyrin }-acetate Similar to instructions 1c), 682 mg (0.5 mmol) of the porphyrin produced under 2b) is reacted with 162 mg (2.0 mmol) of anhydrous sodium acetate and 490 mg of manganese(II)-acetate tetrahydrate in 100 ml of DMF. The product obtained is dissolved in absolute ethanol and precipitated by the addition of absolute diethylether. The green powder is suctioned off by a frit and dried in the vacuum shelf dryer at 60° C. Residues of solvent are removed by drying at the oil pump. 583 mg (79% of theory) of the compound is obtained.

| Analysis: | | | | |
|---|---|---|---|---|
| Calculated: | C 63.49 | H 5.67 | N 7.59 | Mn 3.72 |
| Found: | C 63.28 | H 5.72 | N 7.68 | Mn 3.59 | d) Manganese(III)- {5,10,15,20-tetrakis <[4-carboxylic acid-(2,3-dihydroxy-1-hydroxymethylpropyl)-amide]-phenyl >-porphyrin-acetate Similar to instructions 1d), 560 mg (0.38 mmol) of the manganese complex produced under 2c) is reacted in a mixture of 10 ml of distilled water and 5 ml of glacial acetic acid. The product is obtained as a green foam by freeze drying.

Yield: 427 mg (85.4% of theory).

| Analysis: The manganese detemination is performed by AAS | | | | | |
|---|---|---|---|---|---|
| Calculated: | C 60.27 | H 5.13 | N 8.52 | Mn 4.18 | O 21.90 |
| Found: | C 60.30 | H 5.21 | N 8.49 | Mn 4.15 | |

EXAMPLE 3

Manganese(III)- {5,10,15,20-tetrakis <[4-sulfonic acid-(2,3,4-trihydroxybutyl)-amide]-phenyl >-porphyrin }-acetate a) mesotetra(4-chlorosulfonylphenyl)-porphyrin 2.48 g (2 mmol) of tetrasodium-mesotetra(4-sulfonatophenyl)-porphyrin dodecahydrate (J. Winkelman et al., Cancer Res. 27, 2060, 1967) is suspended in 25 ml of phosphoryl chloride and mixed, excluding moisture, with 1.66 g (8 mmol) of phosphorous pentachloride. Excluding moisture and with stirring, it is heated for 2 hours to 75° C. Then the solvent is drawn off, the residue is codistilled with 1,2-dichloroethane and evaporated in a vacuum to dryness. The product is obtained as a green powder; it is put into the next reaction step without further purification.

b) 5,10,15,20-Tetrakis <{4-sulfonic acid-[2-hydroxyl2-(2,2-diemthyl-1,3-dioxolan-4-yl)-ethyl]-amide }-phenyl >-porphyrin The sulfonyl chloride produced under 3a) is added, with cooling and stirring, to the solution of 1.94 g (12 mmol) of 2- amino-1-(2,2-dimethyl-1,3-dioxolan-4-yl)-ethanol and 8 ml (58 mmol) of triethylamine in 250 ml of dry tetrahydrofuran. It is stirred for 1 hour, the solution is concentrated by evaporation to about 100 ml in a vacuum and it is diluted with dichloromethane, to which some ethanol was added as a solubilizer. The solution is extracted several times with half-strength ammonia to remove portions with free sulfonic acids. Then it is dried over sodium sulfate and evaporated in a vacuum to dryness.

Yield: 1.27 g (42.1% of theory)

| Analysis: | | | | |
|---|---|---|---|---|
| Calculated: | C 57.36 | H 5.48 | N 7.43 | S 8.51 |
| Found: | C 57.02 | H 5.61 | N 7.55 | S 8.36 | c) Manganese(III)-{5,10,15,20-tetrakis<{4-sulfonic acid-[2-hydroxy-2-(2,2-dimethyl-1,3-dioxolan-4-yl)-ethyl]-amide}-phenyl>-porphyrin}-acetate 217 mg (2.64 mmol) of anhydrous sodium acetate is heated in 130 ml of dimethylformamide to 120° C. It is mixed with 1000 mg (0.66 mmol) of the compound produced under 3b) and is heated with stirring to 150° C. To this solution, 647 mg (2.64 mmol) of manganese(II)-acetate tetrahydrate is added, which is associated with foaming. After one hour, the complexing is complete (color change red to green, no more starting material detectable.) After cooling, the solvent is drawn off in a vacuum. The residue is dissolved in ethanol and the solution is filtered. It is concentrated by evaporation to about 30 ml, diluted with 500 ml of chloroform and washed 2 times with distilled water. The organic solution is dried over sodium sulfate and evaporated to dryness. The manganese complex is obtained as a powder.

Yield: 822 mg (76.9% theory).

The manganese content is determined by AAS.

| Analysis: | | | | | |
|---|---|---|---|---|---|
| Calculated: | C 54.87 | H 5.17 | N 6.92 | Mn 3.39 | S 7.92 |
| Found: | C 55.01 | H 5.38 | N 6.69 | Mn 3.37 | S 7.59 | d) Manganese(III)-{5,10,15,20-tetrakis<{4-sulfonic acid-(2,3,4-trihydroxybutyl)-amide}-phenyl>-porphyrin}-acetate 1.29 g (0.8 mmol) of the compound produced under c) is dissolved in 10 ml of glacial acetic acid. The solution is diluted with 10 ml of water. It is heated for 3 hours to 80° C. In the thin film chromatogram, no more starting material can be detected. The solution is evaporated in a vacuum to dryness, the residue is taken up in distilled water and subjected to freeze drying. The product is obtained as a green foam.

Yield: 976 mg (83.4% of theory).

| Analysis: | | | | | | |
|---|---|---|---|---|---|---|
| Calculated: | C 51.03 | H 4.63 | N 7.68 | O 24.12 | Mn 3.76 | S 8.79 |
| Found: | C 50.98 | H 4.70 | N 7.61 | | Mn 3.72 | S 8.73 |

EXAMPLE 4

Manganese(III)-[5,10,15,20-tetrakis(3-carboxylatophenyl)-porphyrin]-acetate, tetrasodium salt a) Mesotetra(3-trifluoromethylphenyl)-porphyrin 8.74 g (50 mmol) of 3-trifluoromethylbenzaldehyde is dissolved in 500 ml of propionic acid and heated to 60° C. Then 3.5 ml (50 mmol) of pyrrole is added and refluxed for an hour with stirring and moisture exclusion. It is left to cool overnight, the solution is evaporated to dryness, the propionic acid residues are removed by codistillation with ethanol, the remainder is taken up in acetic ester/ethanol and crystallized at 4° C. The product is suctioned off, washed with a little acetic acid and dried in a vacuum at 50° C.

Yield: 4.98 g (32.8% of theory) Melting point: >220° C.

b) Mesotetra(3-carboxylatophenyl)-porphyrin, tetrasodium salt 1.02 (1.5 mmol) of mesotetra-(3-trifluoromethylphenyl)-porphyrin is dissolved in 30 ml of concentrated sulfuric acid and heated for 3 hours to 100° C. It is left to cool to room temperature, then poured into 500 ml of ice water and adjusted with 40% sodium hydroxide solution to a pH of 4.5. The forming precipitate is left to deposit and is centrifuged, excluding light. The precipitate is washed with distilled water, dissolved with 0.5N of sodium hydroxide solution and evaporated in a vacuum to dryness. The residue is extracted three times with dry ethanol. The combined solutions are evaporated in a vacuum to dryness.

Remainder: 1.47 g (>100%).

The product is added to the complexing without purification.

c) Manganese(III)-[5,10,15,20-tetrakis(3-carboxylatophenyl)-porphyrin]-acetate, tetrasodium salt 492 mg (6 mmol) of anhydrous sodium acetate is heated to boiling in 70 ml of dimethylformamide. Now 1.47 g (1.5 mmol) of mesotetra(3-carboxylatophenyl)-porphyrin, tetrasodium salt and 1.47 g (6 mmol) of manganese(II)-acetate tetrahydrate are added to the solution. It is refluxed for 3 hours excluding light and with stirring. After cooling, the solvent is drawn off in a vacuum, the remainder is mixed with distilled water and centrifuged. The supernatant solution is decanted, the remainder is suspended in water and again centrifuged. The combined solutions are purified by column chromatography on 300 g of RP silica gel (Merck, RP 18) with water and methanol. After freeze drying, the dark green manganese complex is obtained as foam.

Yield: 1.236 g (83.2% of theory).

| Analysis: The manganese dertermination is performed by AAS. | | | | | |
|---|---|---|---|---|---|
| Calculated: | C 60.62 | H 2.75 | N 5.66 | Mn 5.55 | Na 9.28 | O 16.15 |
| Found: | C 60.58 | H 2.79 | N 5.61 | Mn 5.52 | Na 9.26 | |

EXAMPLE 5

Mesotetrakis{4-[1-carboxylato-2,5,8-tris(carboxylatomethyl)-2,5,8-triazanonyl carbonylamino]-phenyl}-porphyrin-gadolinium(III)-complex, tetrasodium salt a) $N^3$(2,6-dioxomorpholinoethyl)-$N^6$-(ethoxycarbonylmethyl)-3,6-diazaoctanedioic acid A suspension of 21.2 g (50 mmol) of $N^3,N^6$-bis-(carboxymethyl)-$N^9$-(ethoxycarbonylmethyl)-3,6,9-triazaundecanedioic acid (J. Pharm. Sci. 68, 1979, 194) in 250 ml of acetic anhydride is stirred, after the addition of 42.2 ml of pyridine, for three days at room temperature. Then the precipitate is suctioned off, it is washed three times, each time with 50 ml of acetic anhydride and then stirred up for several hours with absolute diethylether. After suctioning off, washing with absolute diethylether and drying in a vacuum at 40° C., 18.0 g (89% of theory) of a white powder with a melting point of 195°-196° C. is obtained.

| Analysis: | | | |
|---|---|---|---|
| Calculated: | C 47.64 | H 6.25 | N 10.42 |
| Found: | C 47.54 | H 6.30 | N 10.22 | b) A solution of 820.6 mg (1 mmol) of mesotetra-(4-aminophenyl)-porphyrin tetrahydrochloride (A. S. Semeikin et al., C.A. 165, 1986, 133611 h) in a mixture of 75 ml of dioxane and 75 ml of distilled water is adjusted with sodium hydroxide solution to a pH of 9. A slight clouding of the solution is eliminated by the addition of 10 ml of dioxane. At 5° C., 2.42 g (6 mmol) of the diethylenetriaminepentaacetic acid-ethyl ester monoanhydride obtained according to example 5a) is added in portions, and the pH is maintained between 8 and 9. After the addition is finished, it is stirred again for 30 minutes. Then the solution is adjusted to pH 10 and left to stand overnight. The solution is now brought to pH 8. By adding 2.88 g (6 mmol) of gadolinium triacetate tetrahydrate in portions, the gadolinium complex is obtained. It is stirred again for an hour, the solution is concentrated by evaporation in a vacuum, taken up in distilled water and centrifuged. The residue is suspended with water and again centrifuged. The combined solutions are evaporated in a vacuum to dryness. The residue is subjected to column chromatography on silica gel. The product is eluted with a dioxane/ammonia mixture, the eluate is then evaporated to dryness, taken up in water, centrifuged and freeze dried. The dark powder is digested with warm DMF, suctioned off, washed with diethylether and dried in a vacuum at 50° C.

Yield: 1.17 g (40.6% of theory).

| Analysis: The gadolinium content is determined by AAS. | | | | | | |
|---|---|---|---|---|---|---|
| Calculated: | C 41.69 | H 3.75 | N 9.72 | Gd 21.83 | Na 3.19 | O 19.99 |
| Found: | C 41.69 | H 3.62 | N 9.68 | Gd 21.75 | Na 3.15 | |

EXAMPLE 6

Manganese(III)-{mesotetrakis-[4-(1-carboxylato-2,5,8-tris(carboxylatomethyl)-2,5,8-triazanonyl-carbonylamino]-phenyl]-porphyrin}-acetate, gadolinium complex, tetrasodium salt 266 mg (0.092 mmol) of the compound produced in example 5 is dissolved in a mixture of 10 ml of glacial acetic acid and 1 ml of distilled water. After the addition of 16 mg (0.190 mmol) of anhydrous sodium acetate it is heated to 80° C., mixed with 47 mg (0.190 mmol) of manganese diacetate tetrahydrate and stirred for 2 hours. No more starting material is shown in the thin film chromatogram. The solution obtained is evaporated in a vacuum to dryness. The residue is taken up in water, made alkaline, centrifuged and the product is purified by chromatogrphy on silica gel RP. The combined solutions are evaporated in a vacuum to dryness. The residue is dissolved in water and subjected to freeze drying. The title compound is obtained as a green foam.

Yield: 238 mg (86.4% of theory).

The metal determination is performed with the Plasma Quad of the company VG Instruments, England.

| Analysis: | | | | | | | |
|---|---|---|---|---|---|---|---|
| Calculated: | C 40.93 | H 3.47 | N 9.36 | Mn 1.84 | Gd 21.02 | Na 3.07 | O 20.37 |
| Found | C 40.88 | H 3.52 | N 9.31 | Mn 1.83 | Gd 20.94 | Na 3.03 | |

EXAMPLE 7

5-{4-[1-Carboxylato-10-oxo-2,5,8-tris(carboxylatomethyl)-2,5,8,11-tetraazatridecylcarbamoyl]-phenyl}-10,15,20-tris(4-carboxylatophenyl)-porphyrin gadolinium complex, tetrasodium salt a)
10,15,20-tris-(4-Carboxyphenyl)-5-{4-[2-(N-benzyloxycarbonylamino)-ethylcarbamoyl]-phenyl}-porphyrin 2.37 g (3 mmol) of mesotetra(4-carboxyphenyl)-porphyrin is dissolved in 200 ml of dimethylformamide and mixed with 153.2 mg (1 mmol) of hydroxybenzotriazole hydrate, 101.2 mg (1 mmol) of triethylamine and 231 mg (1 mmol) of N-benzyloxycarbonyldiaminoethane hydrochloride. It is cooled, excluding moisture, to −10° C. and mixed with stirring with 206.3 mg (1 mmol) of dicyclohexylcarbodiimide. It is stirred for an hour at the low temperature, then allowed to come to room temperature and the reaction is followed with thin film chromatography until no more starting amine can be detected. It is suctioned through a frit, the filtrate is concentrated by evaporation in a vacuum and the residue is divided between a sodium bicarbonate solution and dichloromethane. The organic solution is dried over sodium sulfate, concentrated by evaporation and the residue is subjected to column chromatography on silica gel. The product is eluted with dioxane/aqueous ammonia. It is evaporated in a vacuum to dryness, taken up in distilled water, filtered and the title compound is obtained by careful acidification. It is suctioned off, washed with a little water and dried in a vacuum.

Yield: 661.4 mg (68.4% of theory).

| Analysis: | | | |
|---|---|---|---|
| Calculated: | C 72.04 | H 4.38 | N 8.69 |
| Found: | C 71.93 | H 4.45 | N 8.59 | b)
10,15,20-Tris(4-carboxyphenyl)-5-{4-[(2-amino)-ethylcarbamoyl]-phenyl}-porphyrin, trihydrochloride 4.835 g (5 mmol) of the compound obtained according to 7a) is dissolved in 25 ml of trifluoroacetic acid and left for 48 hours at room temperature. Then the solvent is drawn off in a vacuum. The remainder is concentrated by evaporation twice with ethanolic hydrochloric acid and crystallized by mixing with absolute diethylether. The crystals are drawn off, washed with a little ether and dried over potassium hydroxide in a vacuum.

Yield: 3.973 g (84.6% of theory).

| Analysis: | | | | |
|---|---|---|---|---|
| Calculated: | C 63.94 | H 3.86 | N 8.95 | Cl 11.32 |
| Found: | C 64.05 | H 3.99 | N 8.81 | Cl 11.20 |

Alternative way to produce 7b):

alpha)
10,15,20-Tris(4-carboxyphenyl)-5-{4-[2-(N-t-butyloxycarbonylamino)-ethylcarbamoyl]-phenyl}-porphyrin 2.37 g (3 mmol) of mesotetra(4-carboxyphenyl)-porphyrin is dissolved in 200 ml of dimethylformamide and reacted with 135 mg (1 mmol) of hydroxybenzotriazole, 160.2 mg (1 mmol) of N-t-butyloxycarbonylethylenediamine and 206 mg (1 mmol) of dicyclohexylcarbodiimide similar to example 7a) and worked up. The raw product is purified by column chromatography on silica gel with dioxane/aqueous ammonia as elution agent. The combined fractions containing the product are evaporated in a vacuum to dryness, dissolved in distilled water and filtered. The product is precipitated by acidification. It is suctioned off, washed with water and dried in a vacuum. Yield: 734.3 mg (78.7% of theory)

| Calculated: | C 70.81 | H 4.75 | N 9.01 |
|---|---|---|---|
| Found: | C 70.62 | H 4.80 | N 9.12 | beta)
10,15,20-Tris(4-carboxyphenyl)-5-{4-[(2-amino)-ethylcarbamoyl]-phenyl}-porphyrin, trihydrochloride 933 mg (1 mmol) of the compound produced according to 7 alpha) is dissolved in 10 ml of 2-mole hydrochloric acid in glacial acetic acid and left for 2 hours at room temperature. Then it is evaporated in a vacuum to dryness, the residue is stirred up with ethereal hydrochloric acid, the crystals are suctioned off and rewashed with a little dry ether. The product is dried in a vacuum over potassium hydroxide.

Yield: 781.5 mg (83.2% of theory).

| Analysis: | | | | |
|---|---|---|---|---|
| Calculated: | C 63.94 | H 3.86 | N 8.95 | Cl 11.32 |
| Found: | C 64.07 | H 4.00 | N 8.79 | Cl 11.39 | c) 5-{4-[1-Carboxylato-10-oxo-2,5,8-tris(carboxylatomethyl)-2,5,8,11-tetraazatridecylcarbamoyl]-phenyl}-10,15,20-tris(4-carboxylatophenyl)-porphyrin, heptasodium salt 939 mg (1 mmol) of the amino compound produced according to example 7b) is dissolved in 100 ml of distilled water and adjusted to pH 9.0. It is cooled to 5° C. and, to the stirred solution, there is added in portions 444 mg (1.1 mmol) of diethylenetriaminepentaacetic acid ethyl ester monoanhydride (example 5a) and, by adding sodium hydroxide solution, the pH is maintained between 7.5 and 8.5. After the adding is finished, the pH is adjusted to 10 and the solution is stirred overnight. The product is purified by column chromatography on silica gel RP 18. The portions eluted with methanol are combined, evaporated to dryness, taken up in distilled water and freeze dried.

Yield: 957.6 mg (70.3% of theory).

| Analysis: | | | |
|---|---|---|---|
| Calculated: | C 56.44 | H 3.70 | N 9.25 | Na 11.81 |
| Found: | C 56.30 | H 3.81 | N 9.18 | Na 11.89 | d)
5-{4-[1-Carboxylato-10-oxo-2,5,8-tris(carboxylatomethyl)-2,5,8,11-tetraazatridecylcarbamoyl]-phenyl}-10,15,20-tris(4-carboxylatophenyl)-porphyrin, tetrasodium salt 939 mg (1 mmol) of the amino compound produced according to example 7b) is dissolved in 100 ml of distilled water and the pH is adjusted to 9. It is cooled to 5° C. and, to the stirred solution, there is added in portions 444 mg (1.1 mmol) of diethylenetriaminepentaacetic acid ethyl ester monoanhydride (example 5a), and, by adding sodium hydroxide solution, the pH is maintained between 7.5 and 8.5. After the adding is finished, the pH is adjusted to 10 and the solution is stirred for 2 hours. Now the pH is lowered to 7.5 and 515 mg (1.1 mmol) of gadolinium acetate tetrahydrate is added in portions, it is stirred overnight at room temperature, the solution is adjusted to pH 8 and is purified by column chromatography on silica gel RP. The product is eluted with methanol. The combined solutions are evaporated to dryness, taken up in distilled water and freeze dried.

Yield: 1003.7 mg (69.2% of theory).

| Analysis: | | | | | |
|---|---|---|---|---|---|
| Calculated: | C 53.00 | H 3.47 | Gd 10.84 | N 8.69 | Na 6.34 | O 17.65 |
| Found: | C 52.95 | H 3.51 | Gd 10.73 | N 8.66 | Na 6.30 |

EXAMPLES 8
Manganese(III)-{5-[4-(1-carboxylato-10-oxo-2,5,8-tris-(carboxylatomethyl)-2,5,8,11-tetraazatridecylcarbamoyl)-phenyl]-10,15,20-tris-(4-carboxylatophenyl)-porphyrin}-acetate, gadolinium complex, tetrasodium salt a)
Manganese(III)-{10,15,20-tris-(4-carboxylatophenyl)-5-<-4-[(2-amino)-ethylcarbamoyl]-phenyl>-porphyrin}-acetate, trisodium salt A mixture of 60 ml of glacial acetic acid and 8 ml of distilled water is heated to 80° C., mixed with 328 mg (4 mmol) of anhydrous sodium acetate and with 933 mg (1 mmol) of the monoethylenediamine derivatives of tetracarboxyphenylporphyrin produced in example 7b). Then another 980 mg (4 mmol) of manganese(II)-acetate tetrahydrate is added and it is stirred, excluding light, at 80°-90° C. until thin film chromatography shows no more red fluorescing portions.

The solution is evaporated in a vacuum to dryness, the residue is suspended in water, brought with sodium hydroxide solution to pH 9.0 and centrifuged. The supernatant solution is separated, concentrated by evaporation in a vacuum and subjected to chromatography on silica gel RP. The product is eluted with methanol-/aqueous ammonia. The combined solutions are concentrated by evaporation, taken up in water and subjected to freeze drying. The title compound is obtained as foam.

Yield: 821.1 mg (82.7% of theory).

| Analysis: | | | | | |
|---|---|---|---|---|---|
| Calculated: | C 62.91 | H 3.45 | Mn 5.53 | N 8.46 | Na 6.95 | O 12.70 |
| Found: | C 62.93 | H 3.48 | Mn 5.50 | N 8.41 | Na 6.96 | b)
Manganese(III)-{5-[4-(1-carboxylato-10-oxo-2,5,8-tris-(carboxylatomethyl)-2,5,8,11-tetraazatridecylcarbamoyl)-phenyl]-10,15,20-tris-(4-carboxylatophenyl)-porphyrin}-acetate, heptasodium salt Similar to example 7c), 992.9 mg 1.0 mmol) of the manganese porphyrin produced under example 8a) is reacted with 444 mg (1.1 mmol) of diethylenetriaminepentaacetic acid ethyl ester monoanhydride (example 5a). The conjugate formed is purified by chromatography on silica gel RP 18. The combined solutions are evaporated in a vacuum to dryness, the residue is taken up in water and subjected to freeze drying. The title compound is obtained as foam.

Yield: 1.274 g (86.4% of theory).
The manganese content is determined by AAS.

| Analysis: | | | | | |
|---|---|---|---|---|---|
| Calculated: | C 53.78 | H 3.49 | Mn 3.73 | N 8.55 | Na 10.92 | O 19.54 |
| Found: | C 53.77 | H 3.52 | Mn 3.71 | N 8.50 | Na 10.87 | c)
Manganese(III)-{5-[4-(1-carboxylato-10-oxo-2,5,8-tris-(carboxylatomethyl)-2,5,8,11-tetraazatridecylcarbamoyl)-phenyl]-10,15,20-tris-(4-carboxylatophenyl)-porphyrin}-acetate, gadolinium complex, tetrasodium salt 164 mg (2 mmol) of anhydrous sodium acetate is added to a mixture of 45 ml of glacial acetic acid and 5 ml of water and heated to 80° C. Then 725 mg (0.5 mmol) of the gadolinium complex produced under 7c) is added as well as 490 mg (2 mmol) of manganese(II)-acetate tetrahydrate and it is stirred, excluding light, at 80°-90° C. until the thin film chromatogram shows no more starting material. After cooling, the solution is evaporated in a vacuum to dryness and the residue is taken up in water. The title compound is purified after chromatography on silica gel RP. The product is obtained by freeze drying th aqueous solution.

Yield: 615 mg (78.7% of theory).
Manganese and gadolinium are determined with the Plasma Quad of the company VG Instruments/England.

| Analysis: | | | | | | |
|---|---|---|---|---|---|---|
| Calculated: | C 50.74 | H 3.29 | Gd 10.07 | Mn 3.52 | N 8.07 | Na 5.89 | O 18.43 |
| Found: | C 50.79 | H 3.32 | Gd 10.01 | Mn 3.50 | N 8.03 | Na 5.86 |

Alternative way to produce (c)
alpha) 992.9 mg (1 mmol) of the manganese porphyrin produced under example 8a) is dissolved in 100 ml of distilled water and adjusted to pH 9. It is cooled to 5° C. and, to the stirred solution, there is added in portions 444 mg (1.1 mmol) of diethylenetriaminepentaacetic acid ethyl ester monoanhydride (example 5a), and, by adding sodium hydroxide solution, the pH is maintained between 7.5 and 8.5. After the adding is finished, the pH is adjusted to 10 and the solution is stirred for 2 hours. Then the pH is adjusted to 7.5, 515 mg (1.1 mmol) of gadolinium acetate tetrahydrate is added in portions and it is stirred overnight at room temperature. The pH is then adjusted to 8 and purification is performed by column chromatography on silica gel RP. The title compound is obtained by freeze drying the aqueous solution.

Yield: 1131 mg (72.4% of theory).

| Analysis: | | | | | | |
|---|---|---|---|---|---|---|
| Calculated: | C 50.74 | H 3.29 | Gd 10.07 | Mn 3.52 | N 8.07 | Na 5.89 O 18.43 |
| Found: | C 50.68 | H 3.34 | Gd 10.00 | Mn 3.49 | N 8.01 | Na 5.82 |

EXAMPLE 9

5-{4-[1-Carboxylato-10-oxo-2,5,8-tris-(carboxylatomethyl)-2,5,8,11-tetraazatridecylcarbamoyl]-phenyl}-10,15,20-tris-(4-carboxylatophenyl)-porphyrin dysprosium complex, tetrasodium salt a)
5-{4-[1-Carboxylato-10-oxo-2,5,8-tris-(carboxylatomethyl)-2,5,8,11-tetraazatridecylcarbamoyl]-phenyl}-10,15,20-tris-(4-carboxylatophenyl)-porphyrin heptasodium salt 939 mg (1 mmol) of the amino compound produced in example 7b) is dissolved in 100 ml of distilled water. By adding sodium hydroxide solution, the pH is adjusted to 9.0 and it is cooled to 5° C. Then 444 mg (1.1 mmol) of diethylenetriaminepentaacetic acid ethyl ester monoanhydride (example 5a) is added with stirring in portions and, by adding sodium hydroxide solution, the pH is maintained between 7.5 and 8.5. After the adding is finished, the pH is adjusted to 10 and stirring is performed overnight. The solution is subjected to column chromatography on silica gel RP 18 and the product is eluted with methanol. Evaporation to dryness is performed in a vacuum, the residue is taken up in water and the title compound is obtained by freeze drying.

Yield: 1.186 g (87.1% of theory).

| analysis: | | | | | |
|---|---|---|---|---|---|
| Calculated | C 56.44 | H 3.70 | N 9.25 | Na 11.81 | O 18.79 |
| Found: | C 56.28 | H 3.83 | N 9.20 | Na 11.70 | | b)
5-{4-[1-Carboxylato-10-oxo-2,5,8-tris-(carboxylatomethyl)-2,5,8,11-tetraazatridecylcarbamoyl]-phenyl}-10,15,20-tris-(4-carboxylatophenyl)-porphyrin dysprosium complex, tetrasodium salt 1.362 g (1 mmol) of the complexing agent produced under example 9a is dissolved in 100 of distilled water. To this solution there is added 411.64 mg (1 mmol) of disprosium acetate tetrahydrate in portions, with stirring, and the pH is maintained between 7 and 8 by adding sodium hydroxide solution. It is restirred overnight and purified by column chromatography on silica gel RP 18. The fractions containing product are combined and evaporated in a vacuum to dryness. The residue is taken up in water and subjected to freeze drying. The title compound is obtained as foam.

Yield: 1.221 g (83.9% of theory).

The dysprosium content is determined with the Plasma Quad of the company VG intruments/England.

| Analysis: | | | | | |
|---|---|---|---|---|---|
| Calculated: | C 52.81 | H 3.46 | Dy 11.16 | N 8.66 | Na 6.32 O 12.59 |
| Found: | C 52.86 | H 3.42 | Dy 11.12 | N 8.63 | Na 6.29 |

EXAMPLE 10

Mesotetrakis {-4-[1-carboxylato-2,5,8-tris(carboxylatomethyl)-2,5,8-triazanonylcarbonylamino]-phenyl}-porphyrin, ytterbium complex, tetrasodium salt a) Mesotetrakis {-4-[1-carboxylato-2,5,8-tris(carboxylatomethyl)-2,5,8-triazanonylcarbonylamino]-phenyl}-porphyrin, hexadecane sodium salt A solution of 820.6 mg (1 mmol) of mesotetra-(4-aminophenyl)-porphyrin tetrahydrochloride (A. S. Semeikin et al., C.A. 105, 1986, 133611h) in a mixture of 75 ml of dioxane and 75 ml of distilled water is adjusted to pH 9 with sodium hydroxide solution. The solution is cooled to 5° C. and, with stirring, 2.42 g (6 mmol) of diethylenetriaminepentaacetic acid ethyl ester monoanhydride (example 5a) is added in portions, and the pH is maintained between 8 and 9. After the adding is finished restirring is performed for another 30 minutes. Then the pH is adjusted to 10 and stirring is performed overnight. The solution is subjected to column chromatography on silica gel RP 18 and the product is eluted with methanol. The solution is evaporated in a vacuum to dryness, the residue is taken up in water and the title compound is obtained by freeze drying.

Yield: 1.754 g (69.4% of theory).

| Analysis: | | | | | |
|---|---|---|---|---|---|
| Calculated: | C 47.51 | H 4.07 | N 11.08 | Na 14.55 | O 22.79 |
| Found: | C 47.40 | H 4.12 | N 11.00 | Na 14.59 | | b) Mesotetrakis {-4-[1-carboxylato-2,5,8-tris(carboxylatomethyl)-2,5,8-triaza-4-[nonylcarbonylamino]-phenyl {-porphyrin, ytterbium complex, tetrasodium salt 1.264 g (0.5 mmol) of the complexing agent produced under example 10a) is dissolved in 100 ml of distilled water and mixed in portions, with stirring, with 844.5 mg (2 mmol) of ytterbium acetate tetrahydrate, and the pH is maintained between 7 and 7.5 by adding sodium hydroxide solution. Restirring is performed overnight and the solution is subjected to column chromatography on silica gel RP 18. The fractions containing product are combined, concentrated by evaporation in a vacuum and the residue is dissolved in water. The title compound is obtained by freeze drying.

Yield: 2.609 g (88.5% of theory).

The metal content is determined with the Plasma Quad of the Company VG/England.

| Analysis: | | | | | |
|---|---|---|---|---|---|
| Calculated: | C 40.80 | H 3.49 | Yb 23.51 | N 9.51 | Na 3.12 O 19.56 |

-continued

Analysis:

lated:
Found: C 40.76  H 3.52  Yb 23.48  N 9.47  Na 3.10

EXAMPLE 11

5-{4-<3-[4 - Σ 1-Carboxylato-2,5-bis(carboxylatomethyl)-6-[N,N-bis(-carboxylatomethyl)-aminomethyl]-2,5-diazaheptyl ζ-phenyl]-thioureidoethylcarbamoyl>-phenyl}-10,15,20-tris(4-carboxylatophenyl)-porphyrin gadolinium complex, pentasodium salt 939.2 mg (1 mmol) of the amine produced under example 7b) is dissolved in 50 ml of distilled water. The pH is adjsuted to 9. To this solution is added, in portions, 594.6 mg (1.1 mmol) of 3,6,9-triaza-3,6,9-tris(carboxylatomethyl)-5-(p-isothiocyanatobenzyl)-undecanedioic acid (O. Gansow et al., Inorg. Chem. 25, 2772, 1986), and the pH is maintained by adding sodium hydroxide solution. Stirring is performed at room temperature overnight. The pH is adjusted to 7.5 and, in portions, 447.1 mg (1.1 mmol) of gadolinium acetate tetrahydrate is mixed in, and the pH is maintained constant by adding sodium hydroxide solution. It is restirred for 2 hours and then subjected to column chromatography on silica gel RP 18. The title compound is obtained by freeze drying the aqueous solution.

Yield: 1027 g (62.7% of theory).

Anslysis:

Calcu-  C 52.81  H 3.45  Gd 9.60  N 8.55  Na 7.02  O 16.61  S 1.96
lated:
Found:  C 52.76  H 3.50  Gd 9.56  N 8.49  Na 7.00            S 1.93

EXAMPLE 12

5-{4-[4,7,10-Tris(carboxylatomethyl)-1,4,7,10-tetraazacyclododecan-1-yl metylcarbonylaminoethylcarbamoyl]-phenyl}-10,15,20-tris(4-carboxylatophenyl)-porphyrin, gadolinium complex, trisodium salt 444.9 mg (1.1 mmol) of 1,4,7,10-tetrakiscarboxymethyl-1,4,7,10-tetraazacyclododecane (H. Stetter et al., Tetrahedron 37, 767, 1981) and 445.2 mg (4.4 mmol) of triethylamine are added to 100 ml of dimethylformamide. Excluding moisture, they are cooled to −12° C. and, with stirring, 150.2 mg (1.1 mmol) of chloroformic acid isobutyl ester is instilled so that the temperature does not exceed −10° C. After 30 minutes, the mixture of 939.2 mg (1 mmol) of the amine produced under 7b) and 607.1 mg (6 mmol) of triethylamine are instilled in 25 ml of dimethylformamide so that the temperature does not exceed −10° C. Stirring is performed for 2 hours at the low temperature and then it is allowed to come to room temperature slowly. It is restirred overnight, evaporated in a vacuum to dryness and made alkaline by sodium hydroxide solution. After concentration by evaporation, the residue is taken up in 100 ml of distilled water, the pH is adjusted to 7.5 and, with stirring, it is mixed in portions with 447.1 mg (1.1 mmol) of gadolinium acetate tetrahydrate. It is stirred overnight at room temperature, the product is purified by chromatography on silica gel RP 18. The title compound is obtained as foam by freeze drying the aqueous solution.

Yield: 988.8 mg (67.2% of theory).

Analysis:

Calcu-  C 53.87  H 3.84  Gd 10.89  N 9.52  Na 4.69  O 17.40
lated:
Found:  C 53.81  H 3.91  Gd 10.81  N 9.47  Na 4.63

EXAMPLE 13

Manganese(III)- Σ 5-<4-[4,7,10-tris(carboxylatomethyl)-1,4,7,10-tetraazacyclododecan-1-ylcarbonyl]-phenyl>-10,15,20-tris(4-carboxylatophenyl)-porphyrin ζ -acetate Hexasodium salt Similar to Example 12, 1.806 g (2 mmol) of manganese(III)-[mesotetra-(4-carboxyphenyl)-porphyrin]-acetate, which was obtained according to A. Harriman and G. Porter, J. Chem. Soc. Faraday Trans. II 75 (1979) 1532, is reacted in 100 ml of dimethylformamide with 111.3 mg (1.1 mmol) of triethylamine and 150.3 mg (1.1 mol) of chloroformic acid isobutylester to a mixed anhydride. Then, with temperature not exceeding −10° C., the mixture of 342.4 mg (1 mmol) of 1,4,7-tris(carboxymethyl)-1,4,7,10-tetraazacyclododecane (European patent application publication number 0232751) and 306.6 mg (3 mmol) of triethylene is instilled in 25 ml of dimethylformamide with stirring. It is stirred for 2 hours at the low temperature and then allowed to come slowly to room temperature. It is restirred overnight, converted, as described in example 12, into the sodium salt and the product is purified by chromatography on silica gel RP 18. The title compound is obtained by freeze drying the aqueous solution.

Yield: 935.04 mg (68.6% of theory).

Analysis:

Calcu-  C 56.40  H 3.62  Mn 4.03  N 8.22  Na 10.12  O 17.61
lated:
Found:  C 56.20  H 3.70  Mn 4.01  N 8.16  Na 10.17

EXAMPLE 14

5,10,15-Tris{4-[1-carboxylato-10-oxo-2,5,8-tris(carboxylatomethyl)-2,5,8,11-tetraazatridecylcarbamoyl]-phenyl}-20-(4-carboxylatophenyl)-porphyrin, gadolinium complex, tetrasodium salt a)

5,10,15-Tris{4-[2-(t-butyloxycarbonylamino)-ethylcarbamoyl]-phenyl}-20-(4-carboxylatophenyl)-porphyrin, sodium salt and
mesotetrakis{-4-[2-(t-butyloxycarbonylamino)-ethylcarbamoyl]-phenyl}-porphyrin 4.74 g (6 mmol) of mesotetra(4-carboxyphenyl)-porphyrin is dissolved in 400 ml of dimethylformamide and mixed with 2.757 g (18 mmol) of hydroxybenzotriazole hydrate, 2.884 g (18 mmol) of N-t-butyloxycarbonylethylenediamine and 3.714 g (18 mmol) of dicyclohexylcarbodiimide and reacted and worked up similar to example 7 alpha). The raw product is purified by column chromatography on silica gel. Isopropanol acts as the eluent. The tetrasubstitution product is obtained from the first runnings by concentration by evaporation in a vacuum and the trisubstitution product is obtained from the more polar fractions.

Mesotetrakis{-4-[2-(t-butyloxycarbonylamino)-ethyl-carbamoyl]-phenyl}-porphyrin

Yield: 1.819 g (26.7% of theory).

| Analysis: | | | | |
|---|---|---|---|---|
| Calculated: | C 71.32 | H 4.92 | N 11.09 | O 12.67 |
| Found: | C 71.24 | H 4.99 | N 11.02 | |

5,10,15-Tris{4-[2-(t-butyloxycarbonylamino)-ethylcarbamoyl]phenyl}-20-(4-carboxylatophenyl)-porphyrin, sodium salt Yield: 3.914 g (48.7% of theory).

| Analysis: | | | | | |
|---|---|---|---|---|---|
| Calculated: | C 69.95 | H 4.74 | N 10.46 | Na 1.72 | O 13.14 |
| Found: | C 70.01 | H 4.81 | N 10.49 | Na 1.70 | | b)
5,10,15-Tris{4-[1-carboxylato-10-oxo-2,5,8-tris(carboxylatomethyl)-2,5,8,11-tetraazatridecylcarbamoyl]-phenyl}-20-(4-carboxylatophenyl)-porphyrin gadolinium complex, tetrasodium salt 1.339 g (1 mmol) of the trisamide produced under example 14a) is dissolved in 50 ml of 2 molar hydrochloric acid in glacial acetic acid and left for 2 hours at room temperature. It is evaporated to dryness in a vacuum, acetic acid residues are distilled off azeotropically with distilled water and the residue is taken up in 100 ml of water. The pH is adjusted with sodium hydroxide solution to 9, it is cooled to 0° C. and mixed in portions with 1.331 g (3.3 mmol) of DTPA monoanhydride (example 5a), and the pH is maintained constant by adding sodium hydroxide solution. It is restirred for an hour, then brought to pH 10 and left to stand overnight. The pH is then lowered to 7.5 by adding hydrochloric acid and 1.341 g (3.3 mmol) of gadolinium acetate tetrahydrate is added in portions. It is restirred overnight and the complex is purified by column chromatography on silica gel RP 18. The title compound is eluted with methanol/ammonia. The fractions containing product are evaporated to dryness in a vacuum, taken up in water and the title compound is obtained by freeze drying.

Yield: 1.857 g (71.6% of theory).

| Analysis: | | | | | |
|---|---|---|---|---|---|
| Calculated: | C 44.46 | H 3.81 | Gd 18.19 | N 10.26 | Na 3.55 |
| | O 19.74 | | | | |
| Found: | C 44.40 | H 3.87 | Gd 18.09 | N 10.19 | Na 3.50 |

EXAMPLE 15

Mesotetrakis{4-[1-carboxylato-10-oxo-2,5,8-tris(carboxylatomethyl)-2,5,8,11-tetraazatridecylcarbamoyl]-phenyl}-porphyrin, gadolinium complex, tetrasodium salt Under the conditions of example 14b), 757.8 mg (0.5 mmol) of the tetramide produced under 14a) in 40 ml of 2 molar hydrochloric acid is broken down in glacial acetic acid and then reacted in 100 ml of distilled water with 1.008 mg (2.5 mmol) of DTPA monoanhydride (example 5a) and then with 1.016 g (2.5 mmol) of gadolinium acetate into gadolinium complex. The title compound is obtained by freeze drying.

Yield: 1.174 g (74.3% of theory).

| Analysis: | | | | | |
|---|---|---|---|---|---|
| Calculated: | C 42.55 | H 3.76 | Gd 19.90 | N 10.63 | Na 2.91 O 20.24 |
| Found: | C 42.60 | H 3.81 | Gd 19.89 | N 10.58 | Na 2.87 |

EXAMPLE 16

Manganese(III)-{mesotetrakis[4-(1-carboxylato-10-oxo-2,5,8-tris(carboxylatomethyl)-2,5,8,11-tetraazatridecyl-carbamoyl)-phenyl]-porphyrin}-acetate, gadolinium complex, tetrasodium salt Under the conditions of example 8c), 1.581 g (0.5 mmol) of the gadolinium complex produced according to example 15 is reacted in a mixture of 63 ml of glacial acetic acid and 7 ml of water with 656.2 mg (8 mmol) of anhydrous sodium acetate and 1.961 g (8 mmol) of manganese(II)-acetate tetrahydrate. It is worked up in a similar way and the title compound is obtained by freeze drying.

Yield: 1.311 g (80% of theory).

| Analysis: | | | | | |
|---|---|---|---|---|---|
| Calculated: | C 41.83 | H 3.66 | Gd 19.22 | Mn 1.68 | N 10.27 Na 2.81 |
| | O 20.53 | | | | |
| Found: | C 41.78 | H 3.71 | Gd 19.19 | Mn 1.67 | N 10.25 Na 2.77 |

EXAMPLE 17

Manganese(III)-[5,10,15,20-tetrakis(4-methoxy-3-sulfonatophenyl)-porphyrin]-acetate, tetrasodium salt a)
5,10,15,20-tetrakis(4-methoxy-3-sulfonatophenyl)-porphyrin, tetrasodium salt 1.27 g (1.7 mmol) of mesotetra-(4-methoxyphenyl)-porphyrin (Aldrich Chemie GmbH, D-7924 Steinheim) is dissolved in 35 ml of concentrated sulfuric acid and heated to 100° C. for 2 hours. It is then poured on ice water and brought to pH 9.5 with 40% sodium hydroxide solution. The solution is evaporated to dryness. The residue is decocted several times with methanol. The combined solutions are evaporated to dryness in a vacuum.

Yield: 1.43 g (73.6% of theory).

| Analysis: | | | | |
|---|---|---|---|---|
| Calculated: | C 50.44 | H 2.99 | N 4.90 | S 11.22 |
| Found: | C 50.03 | H 3.06 | N 4.63 | S 10.88 | b)
Manganese(III)-[5,10,15,20-tetrakis(4-methoxy-3-sulfonatophenyl)-porphyrin]-acetate, tetrasodium salt 121 mg (1.48 mmol) of anhydrous sodium acetate is poured into 70 ml of dimethylformamide and heated to 150° C. Then 1.28 g (1.1 mmol) of 5,10,15,20-tetrakis(4-methoxy-3-sulfonatophenyl)-porphyrin, tetrasodium salt and finally 882 mg (3.6 mmol) of manganese(II)-acetate tetrahydrate are added and refluxed with stirring for an hour. Since the thin film chromatogram still shows starting material, 760 mg (3.10 mmol) of manganese acetate and 255 mg (3.1 mmol) of sodium acetate are added in portions. It is heated for a total of 10 hours, until the starting material has disappeared, and only the manganese complex can still be detected in the thin film chromatogram. The solvent is drawn off in a vacuum, the residue is taken up with water, brought to pH 9 with sodium hydroxide solution and centrifuged. The excess is separated. The precipitate is mixed with water and again centrifuged. The excesses are combined, concentrated by evaporation and subjected to column chromatography on silica gel RP 18. After a first running with water, the product is eluted with methanol. The solution is concentrated by evaporation in a vacuum, the residue is then dissolved in distilled water and subjected to freeze drying. The product is obtained as a green foam.

Yield: 1.082 g (78.4% of theory).

| Analysis: | | | | | |
|---|---|---|---|---|---|
| Calcu- | C 47.85 | H 2.81 | Mn 4.38 | N 4.46 | Na 7.38 | O 22.95 |
| lated: | S 10.22 | | | | |
| Found: | C 47.81 | H 2.84 | Mn 4.36 | N 4.42 | Na 7.30 | |
| | S 10.19 | | | | |

The manganese content is determined by AAS.

EXAMPLE 18

Manganese(III)-[5,10,15,20-tetrakis(4-fluoro-3-sulfonatophenyl)-porphyrin]-acetate tetrasodium salt a)
5,10,15,20-tetrakis(4-fluoro-3-sulfonatophenyl)-porphyrin, tetrasodium salt 1.373 g (2 mmol) of mesotetra(4-fluorophenyl)-porphyrin (J. B. Kim et al., J. Amer. Chem. Soc. 94, 3986, 1972) is dissolved in 30 ml of concentrated sulfuric acid and heated to 100° C. for 5 hours. Then it is poured on 500 ml of ice water, adjusted to pH 7 with 40% sodium hydroxide solution and evaporated to dryness in a vacuum. The residue is taken up in water and chromatographed over silica gel RP 18. The title compound is obtained as foam by freeze drying the aqueous solution.

Yield: 1.736 g (79.2% of theory).

| Analysis: | | | | | |
|---|---|---|---|---|---|
| Calcu- | C 48.23 | H 2.02 | F 6.93 | N 5.20 | Na 8.39 | O 17.52 |
| lated: | S 11.70 | | | | |
| Found: | C 48.27 | H 2.08 | F 6.88 | N 5.16 | Na 8.41 | |
| | S 11.65 | | | | | b)
Manganese(III)-[5,10,15,20-tetrakis(4-fluoro-3-sulfonatophenyl)-porphyrin]-acetate tetrasodium salt Similar to example 17b), 1.644 g (1.5 mmol) of the sulfonic acid prepared under a) is reacted with a total of 554 mg (6.75 mmol) of anhydrous sodium acetate and 2.48 g (10.12 mmol) of manganese(II)-acetate tetrahydrate in 80 ml of dimethylformamide. It is worked up as described under 17b) and purified by column chromatography on silica gel RP 18. The title compound is obtained as foam.

Yield: 1.410 g (77.9% of theory).

| Analysis: | | | | | |
|---|---|---|---|---|---|
| Calcu- | C 45.78 | H 1.92 | F 6.30 | Mn 4.55 | N 4.64 | Na 7.62 |

| -continued | | | | | |
|---|---|---|---|---|---|
| Analysis: | | | | | |
| lated: | S 10.63 | O 18.56 | | | |
| Found: | C 45.73 | H 1.96 | F 6.25 | Mn 4.52 | N 4.68 | Na 7.66 |
| | S 10.59 | | | | |

EXAMPLE 19

Manganese(III)-[5,10,15,20-tetrakis(4-fluoro-3-carboxylatophenyl)-porphyrin]-acetate, tetrasodium salt a) Mesotetrakis(4-fluoro-3-trifluoromethyl)-porphyrin 9.61 g (50 mmol) of 4-fluoro-3-trifluoromethyl-benzaldehyde is reacted with 3.5 ml (50 mmol) of pyrrole in 500 ml of propionic acid under the conditions of example 4a). The title compound is obtained as a dark powder.

Yield: 3.039 g (31.7% of theory).

| Analysis: | | | | |
|---|---|---|---|---|
| Calculated: | C 60.14 | H 2.31 | F 31.71 | N 5.84 |
| Found: | C 60.08 | H 2.36 | F 31.66 | N 5.80 | b)
Mesotetrakis-(4-fluoro-3-carboxylatophenyl)-porphyrin, tetrasodium salt

Similar to example 4b), 959 mg (1 mmol) of the porphyrin produced under 19a) is reacted in 25 ml of concentrated sulfuric acid. Working up and purification are performed in a similar way. The title compound is obtained as a green powder by freeze drying the aqueous solution.

Yield: 787.2 mg (82.8% of theory).

| Analysis: | | | | | |
|---|---|---|---|---|---|
| Calcu- | C 60.64 | H 2.33 | F 7.99 | N 5.89 | Na 9.67 | O 13.46 |
| lated: | | | | | |
| Found: | C 60.60 | H 2.36 | F 7.94 | N 5.85 | Na 9.61 | | c)
Manganese(III)-[5,10,15,20-tetrakis(4-fluoro-3-sulfonatophenyl)-porphyrin]-acetate tetradodium salt Similar to example 17b), 475.3 mg (0.5 mmol) of the porphyrin produced under 19b) is reacted with a total of 189 mg (2.3 mmol) of anhydrous sodium acetate and 1.225 g (5 mmol) of manganese(II)-acetate tetrahydrate in 50 ml of dimethylformamide. Working up is performed as described and purification is performed by column chromatography on silica gel RP 18. The title compound is obtained by freeze drying the aqueous solution.

Yield: 424.5 mg (79.9% of theory).

| Analysis: | | | | | |
|---|---|---|---|---|---|
| Calcu- | C 56.52 | H 2.18 | F 7.15 | Mn 5.17 | N 5.27 | Na 8.65 |
| lated: | O 15.06 | | | | |
| Found: | C 56.50 | H 2.16 | F 7.11 | Mn 5.13 | N 5.23 | Na 8.61 |

EXAMPLE 20

Manganese(III)-[5,10,15,20-tetrakis(3,5-dicarboxylatophenyl)-porphyrin]-acetate, octasodium salt a)
Mesotetrakis-[3,5-bis(trifluoromethyl)-phenyl]-porphyrin Under the conditions of example 4a), 3.5 ml (50 mmol) of pyrrole is reacted with 12.11 g (50 mmol) of 3,5-bis(trifluoromethyl)-benzaldehyde in 500 ml of propionic acid. The porphyrin is obtained as a dark powder.

Yield: 6.628 g (28.6% of theory).

| Analysis: | | | | |
|---|---|---|---|---|
| Calculated: | C 53.90 | H 1.91 | F 39.35 | N 4.84 |
| Found: | C 53.83 | H 1.94 | F 39.30 | N 4.86 | b) Mesotetrakis-[3,5-dicarboxylatophenyl]-porphyrin, octasodium salt 1.159 g (1 mmol) of the porphyrin produced under 20a) is dissolved in 30 ml of concentrated sulfuric acid and heated to 100° C. for 4 hours. Then it is cooled, poured on 500 ml of ice water, the pH is adjusted to 7 with 40% sodium hydroxide solution, evaporated to dryness in a vacuum and the residue is taken up in water. It is chromatographed on silica gel RP 18. The title compound is obtained by freeze drying the aqueous solution.

Yield: 963.3 mg (84.3% of theory).

| Analysis: | | | | | |
|---|---|---|---|---|---|
| Calculated: | C 54.66 | H 1.94 | N 4.90 | Na 16.10 | O 22.40 |
| Found: | C 54.60 | H 2.00 | N 4.86 | Na 16.15 | | c)
Manganese(III)-[5,10,15,20-tetrakis(3,5-dicarboxylatphenyl)-porphyrin]-acetate, octasodium salt Similar to example 17b), 1.143 g (1 mmol) of the porphyrin produced under 20b) is reacted with a total of 377 mg (4.6 mmol) of anhydrous sodium acetate and 2.451 g (10 mmol) of manganese(II)-acetate tetrahydrate in 60 ml of dimethylformamide. It is worked up as described, the product is purified by column chromatography on silica gel RP 18 and the title compound is obtained as foam by freeze drying.

Yield: 1.013 g (80.7% of theory).

| Analysis: | | | | | |
|---|---|---|---|---|---|
| Calculated: | C 51.70 | H 1.85 | Mn 4.38 | N 4.47 | Na 14.66 | O 22.95 |
| Found: | C 51.66 | H 1.89 | Mn 4.35 | N 4.43 | Na 14.61 | |

EXAMPLE 21

Mesotetrakis{3-[1-carboxylato-2,5,8-tris-(carboxylatomethyl)-2,5,8-triazanonylcarbonylamino]-4-metehylphenyl}-porphyrin, gadolinium complex, tetrasodium salt a) Mesotetrakis-(4-methyl-3-nitrophenyl)-porphyrin 1.342 g (2 mmol) of 5,10,15,20-(4-methylphenyl)-porphyrin (A. S. Semeikin et al., Klim. Geterotsikl. Soedin. 1986, 6, 798) is dissolved in 50 ml of concentrated sulfuric acid. 864 mg (9.6 mmol) of 70% nitric acid is instilled with stirring in the solution, cooled to 0° C., so that the temperature is maintained. It is left for 2 hours at 0° C. and then stirred another 2 hours at room temperature. Then it is poured on 500 ml of ice water, neutralized with sodium hydroxide solution and the solid matter is filtered off. It is washed with water, dried in a vacuum and the title compound is obtained as a dark powder.

Yield: 1.152 g (67.7% of theory).

| Analysis: | | | | |
|---|---|---|---|---|
| Calculated: | C 67.76 | H 4.03 | N 13.17 | O 15.04 |
| Found: | C 67.72 | H 4.08 | N 13.13 | | b) Mesotetrakis-[3-amino-4-methylporphyrin]

5.352 g (6.29 mmol) of the nitro compound produced under 21a) is suspended in 300 ml of concentratd hydrochloric acid and heated to 70°-80° C. With stirring, now in 30 minutes there is added 30.0 g (133 mmol) of tin(II)-chloride dihydrate. It is permitted to cool, mixed with 300 ml of water, the percipitate is centrifuged off, it is rewashed with half-strength hydrochloric acid, the precipitate is dissolved in 2 liters of water, the green solution is filtered and neutralized with ammonia. The precipitated solid matter is washed with water. The solid matter is dissolved in ethanol and purified by column chromatography on silica gel. Dioxane/aqueous ammonia acts as eluent. The fractions containing product are evaporated to dryness in a vacuum, taken up in ethanol, filtered and again evaporated to dryness. The title compound is obtained as foam.

Yield: 3.168 g (68.9% of theory).

| Analysis: | | | |
|---|---|---|---|
| Calculated: | C 78.88 | H 5.79 | N 15.35 |
| Found: | C 78.80 | H 5.86 | N 15.30 | c)
Mesotetrakis-{3-[1-carboxylato-2,5,8-tris-(carboxylatomethyl)-2,5,8-triazanonylcarbonylamino]-4-methylphenyl}-porphyrin, gadolinium complex, tetrasodium salt Similar to the instructions for example 5b), 730.9 mg (1 mmol) of the tetraamino compound produced under 21b) is dissolved in a mixture of 75 ml of dioxane and 95 ml of distilled water and reacted with 2.42 g (6 mmol) of DTPA monanhydride. The complexing agent thus obtained is converted into the gadolinium complex with 2.88 g (6 mmol) of gadolinium acetate tetrahydrate. Working up and purification are performed as described in example 5. The title compound is obtained by freeze drying the aqueous solution.

Yield: 1.686 g (57.4% of theory).

| Analysis: | | | | | |
|---|---|---|---|---|---|
| Calculated: | C 42.53 | H 3.78 | Gd 21.42 | N 9.54 | Na 3.13 | O 19.61 |
| Found: | C 42.48 | H 3.82 | Gd 21.36 | N 9.50 | Na 3.09 | |

EXAMPLE 22

Manganese(III)-{meso-tetrakis<3-(1-carboxylato-2,5,8-tris-(carboxylatomethyl)-2,5,8-triiazanonylcarbonyl-methyl)-4-methylphenyl>-porphyrin}-acetate, gadolinium complex, tetrasodium salt Analogously to example 5, 1.469 g (0.5 mmol) of the gadolinium complex produced under 21c) in a mixture of 60 ml of glacial acetic acid and 6 ml of distilled water is reacted with 205.1 mg (2.5 mmol) of anhydrous sodium acetate and 612.7 mg (2.5 mmol) of manganese(II) acetate tetrahydrate and worked up. After freeze-drying of the aqueous solvent, the title compound is obtained as a foam.

Yield: 1.262 g (82.8% of theory).

| Analysis: | | | | | |
|---|---|---|---|---|---|
| Calculated: | C 41.76 | H 3.67 | Gd 20.63 | H 1.80 | N 9.19 |
| | Na 3.02 | O 19.94 | | | |
| Found: | C 41.70 | H 3.76 | Gd 20.56 | H 1.79 | N 9.13 |
| | Na 2.99 | | | | |

EXAMPLE 23

Manganese(III)-{5- Σ 4[5-<43-methoxy-tritetracontakis (ethyleneoxy)>-4-oxo-3-aza-pentylcarbamoyl]-phenyl ζ -10,15,20-tris(carboxyatophenyl)porphyrin}-acetate, trisodium salt a)

2-<43-Methoxy-tritetracontakis(ethyleneoxy)>-acetic acid-t-butyl ester 19 g (10 mmol) of monomethoxypolyethylene glycol (produced according to Synthesis 1979, 123) (molecular weight 1900 D) is dissolved in 400 ml of dry benzene and mixed with 800 mg (20 mmol) of powdered sodium hydroxide solution. It is stirred for 30 minutes at room temperature, then warmed to 45° C. and 1.95 ml (12 mmol) of bromoacetic acid t-butyl ester in 20 ml benzene is instilled in it in 2 hours. It is stirred for 3 hours at 45° C. and restirred for one hour at 60° C. Then it is allowed to cool, suctioned off from the solid and washed twice with 50 ml of benzene each time. The solvent is removed in a vacuum, the residue is dried in a vacuum at 40° C.

Yield: 17.609 g (86.3% of theory).

| Analysis: | | | |
|---|---|---|---|
| Calculated: | C 54.74 | H 9.19 | O 36.07 |
| Found: | C 54.69 | H 9.23 | | b) Manganese(III)-{5- Σ 4-[5-<43-methoxy-tritetracontakis (ethyleneoxy)>-4-oxo-3-azapentylcarbamoyl]-phenyl ζ -10,15,20-tris-(carboxylatphenyl]-porphyrin}-acetate, trisodium salt.

2.041 g (1 mmol) of the ester produced under a) is stirred in 60 ml of trifluoroacetic acid for 15 minutes at room temperature. Then the solvent is drawn off in a vacuum, the residue is suspended in 50 ml of toluene and again evaporated to dryness in vacuum. The residue is taken up in 150 ml of dimethylformamide, mixed with 111.3 mg (1.1 mmol) of triethylamine and cooled with moisture exclusion to −12° C. With stirring, 150.2 mg (1.1 mmol) of chloroformic acid isobutylester is instilled now so that the temperature does not exceed −10° C. After 30 minutes, 2.041 g (1 mmol) of the amino compound produced according to example 8a) in 25 ml of dimethylformamide is instilled and the temperature does not exceed −10° C. It is stirred at the low temperature for 2 hours and then the cooling is removed, so that the temperature slowly reaches room temperature. It is restirred overnight, evaporated to dryness in a vacuum, the residue is stirred up with ether and the solid matter is suctioned off. The procedure is repeated and the residue is dried in a vacuum at 50° C. The title compound is obtained as a dark powder.

Yield: 2.338 g (78.2% of theory).

| Analysis: | | | | | | |
|---|---|---|---|---|---|---|
| Calculated: | C 56.89 | H 7.11 | Mn 1.85 | N 2.82 | Na 2.32 | O 29.02 |
| Found: | C 56.81 | H 7.16 | Mn 1.84 | N 2.80 | Na 2.35 | |

EXAMPLE 24

Production of a contrast medium for use in nuclear medicine with $^{111}$In 2.948 mg (2 micromol) of the compound described in example 8b is dissolved in 3 ml of sterile, pyrogen-free 0.1 m citrate buffer (pH 5.8). The solution is filtered over a millipore filter (0.2 microns) into a multivial and mixed with 0.1 ml of a physiological common salt solution containing 1.3 mCi of $^{111}$In Cl$_3$. The solution is ready for use.

EXAMPLE 25

Production of a contrast medium for use in nuclear medicine with $^{99m}$Tc.

2.211 mg (1.5 micromol) of the compound described in example 8b is dissolved in 1.5 ml of sterile, distilled water and mixed with 0.26 mg of sodium hydrogensulfite (1.5 micromol). After the addition of 0.1 n of hydrochloric acid until pH 5.8, the solution is poured over a millipore filter (0.2 microns) and filled into a multivial with nitrogen gassing. After the addition of 0.5 ml of a physiological common salt solution that contains 5.0 mCi of technetium ($^{99m}$Tc)-pertechnetate, a solution ready for use is obtained.

EXAMPLE 26

Production of a contrast medium for NMR diagnosis 45.5 g (35 mmol) of the compound described in example 1d is dissolved to neutrality in 500 ml of a sterile and pyrogen-free buffer solution (0.1 m sodium hydrogencarbonate) with the addition of 500 mg of the calcium disodium salt of ethylenediaminetetraacetic acid and with the introduction of carbon dioxide. The solution is filtered sterile and poured in 50 ml portions into bottles.

EXAMPLE 27

Production of a contrast medium for NMR diagnosis 50.75 g (35 mmol) of the compound described in example 7d is dissolved to neutrality in 500 ml of a sterile and pyrogen-free buffer solution (0.1 m sodium hydrogencarbonate) with the addition of 500 mg of the calcium disodium salt of ethylenediaminetetraacetic acid and by gassing with carbon dioxide. The solution, filtered sterile, is poured into multivials in 50 ml portions.

EXAMPLE 28

Production of a contrast medium for NMR diagnosis 54.60 g (35 mmol) of the compound described in example 8c is dissolved to neutrality in 500 ml of a sterile and pyrogen-free buffer solution (0.1 m sodium hydrogencarbonate) with the addition of 500 mg of the calcium disodium salt of ethylenediaminetetraacetic acid and with carbon dioxide gassing. The solution, filtered sterile, is poured into vials in 50 ml portions.

EXAMPLE 29

Production of a contrast medium for X-ray diagnosis 25.76 g (8.75 mmol) of the compound described in example 10 is dissolved to neutrality in 500 ml of a sterile and pyrogen-free buffer solution (0.1 m sodium hydrogencarbonate) with the addition of 500 mg of the calcium disodium salt of ethylenediaminetetraacetic acid and with carbon dioxide gassing. The solution, filtered sterile, is poured into vials in 50 ml portions.

EXAMPLE

Manganese(III)-[5,10,15,20-tetrakis(4-isopropyl-3-sulfonatophenyl)-porphyrin]-acetate a) 5,10,15,20-Tetrakis(4-isopropylphenyl)-porphyrin Under the conditions of example 4a, 14.82 g (100 mmol) of 4-isopropylbenzaldehyde is reacted with 6.92 ml (100 mmol) of pyrrole in 300 ml of propionic acid. The solution is evaporated to dryness in a vacuum. The residue is heated with 200 ml of ethanol quickly to boiling. It is left to cool slowly, the title compound is suctioned off, washed with a little ethanol and dried at 50° C. in a vacuum.

Yield: 4.40 g (22.5% of theory).

| Analysis: | | | |
|---|---|---|---|
| Calculated: | C 85.89 | H 6.95 | N 7.15 |
| Found: | C 85.77 | H 7.01 | N 7.06 | b)
5,10,15,20-tetrakis(4-isopropyl-3-sulfonatophenyl)-porphyrin, tetrasodium salt.

Similar to example 18a, 2.0 g (2.6 mmol) of the porphyrin produced under 30a) is dissolved in 140 ml of concentrated sulfuric acid and stirred for 2 hours at 150° C. It is permitted to cool to room temperature, poured over 1 liter of ice water and brought to pH 6.4 with 40% sodium hydroxide solution. The solution is evaporated to dryness in a vacuum, extrated with hot methanol and the filtrate is evaporated to dryness. The residue is purified by chromatography on silica gel with ethanol/ammonia as eluent. The title compound is isolated as a violet solid.

Yield: 2.33 g (75.2% of theory).

| Analysis: | | | | | | |
|---|---|---|---|---|---|---|
| Calculated: | C 56.46 | H 4.23 | N 4.70 | Na 7.72 | O 16.12 | S 10.77 |
| Found: | C 56.34 | H 4.31 | N 4.62 | Na 7.79 | | S 10.82 | c)
Manganese(III)-[5,10,15,20-tetrakis(4-isopropyl-3-sulfonatophenyl)-porphyrin]-acetate, tetrasodium salt 3.34 g (2.8 mmol) of the porphyrin produced under example 30b is dissolved in 500 ml of dimethylformamide and heated to boiling. Then 919 mg (11.2 mmol) of sodium acetate and 2.75 g (11.2 mmol) of manganese(II)-acetate tetrahydrate are added and it is refluxed for 4 hours with stirring. After cooling, it is evaporated to dryness in vacuum. It is dissolved in 1 molar hydrochloric acid and the solution is instilled in cooled sodium hdyroxide solution. The solution, adjusted to pH 7, is concentrated in a vacuum. The title compound is obtained by chromatography on silica gel RP 18 with methanol/ammonia as eluent. After freeze drying the aqueous solution, a green powder is obtained.

Yield: 2.67 g (73.2% of theory).

| Analysis: | | | | | | |
|---|---|---|---|---|---|---|
| Calculated: | C 53.46<br>S 9.84 | H 3.94 | Mn 4.22 | N 4.30 | Na 7.06 | O 17.19 |
| Found: | C 53.35<br>S 9.73 | H 4.01 | Mn 4.19 | N 4.24 | Na 7.12 | |

EXAMPLE 31

Manganese(III)-[5,10,15,20-tetrakis-(4-(2-hydroxyethyleneoxy)-3-sulfonatophenyl)-porphyrin]-acetate, tetrasodium salt a)
5,10,15,20-Tetrakis(4-hydroxy-3-sulfonatophenyl)-porphyrin, tetrasodium salt 2.715 g (4 mmol) of 5,10,15,20-tetrakis(4-hydroxyphenyl)-porphyrin (produced according to G. A. Ihamkochyan et al., Khim. Geterotrikl. Soedin, 1987 (2 ) 221) dissolved in 120 ml of concentrated sulfuric acid and, with stirring and stopping off with nitrogen, is stirred for 4 hours at 80° C. After cooling, it is poured on ice water, adjusted to pH 6.0 with 40% sodium hydroxide solution and evaporated to dryness in a vacuum. The residue is extracted with methanol. From the methanol solution, the title compound is obtained by concentration by evaporation in a vacuum. It is reacted without further purification.

b)
5,10,15,20-tetrakis-[4-(2-hydroxyethyleneoxy)-3-sulfonatophenyl]-porphyrin, tetrasodium salt The porphyrin obtained under example 31a is dissolved in a mixture of 40 ml of water and 20 ml of dioxane. It is mixed with 2.25 g (18 mmol) of 2-bromoethanol and 4.5 ml of 4 molar sodium hydroxide solution (18 mmol) and stirred, with stopping off with nitrogen, for 2 days at room temperature. Then the pH of the solution is adjusted to 6 and it is evaporated to dryness in a vacuum. The residue is purified by chromatography on silica gel with methanol/ammonia as eluent. The title compound is obtained as a violet foam.

Yield: 3.22 g (63.7% of theory).

| Analysis: | | | | | | |
|---|---|---|---|---|---|---|
| Calculated: | C 49.37 | H 3.51 | Na 7.27 | N 4.43 | O 25.29 | S 10.14 |

| Analysis: | | | | | |
|---|---|---|---|---|---|
| Found: | C 49.24 | H 3.60 | Na 7.35 | N 4.36 | S 10.02 | c)

Manganese(III)-<5,10,15,20-tetrakis-[4-(2-hydroxyethyleneoxy)-3-sulfonatophenyl)-porphyrin>-acetate, tetrasodium salt 1.898 g (1.5 mmol) of the sulfonic acid produced under 31b is reacted in 10 ml of dimethylformamide with a total of 554 mg (6.75 mmol) of anhydrous sodium acetate and 2.48 g (10.12 mmol) of manganese(II)-acetate tetrahydrate similar to example 17b. It is worked up as described under 17b and purified by column chromatography on silica gel RP 18. The title compound is obtained as foam.

Yield: 1.196 g (57.8% of the title compound).

| | Analysis: | | | | | |
|---|---|---|---|---|---|---|
| Calcu-lated: | C 47.03 S 9.30 | H 3.44 | Mn 3.98 | N 4.06 | Na 6.67 | O 25.52 |
| Found: | C 47.11 S 9.25 | H 3.50 | Mn 3.95 | N 4.01 | Na 6.71 | |

Determination of cell assimilation of porphyrins

The complex compounds described in examples 4 and 17 are tested; for comparison, manganese(III)-[5,10,15,20-tetrakis(4-sulfonatophenyl)-porphyrin (Mn-TPPS), considered a standard (N. J. Patronas et al., Cancer Treatment Reports 70, 391, 1986) was selected.

Performance of test $1 \times 10^7$ HT 29 cells (colon carcinoma) in 8 ml of RPMI/164c medium is mixed with 0.4 ml of the respective porphyrin solution (25 mg/5 ml water). 6 hours of incubation at 37° C. and carbon dioxide and oxygen gassing follow. Then to each sample there is added 3 ml of 16% aqueous trypsine solution, to separate the cells from the walls of the incubation vessel. The cells are then centrifuged off (1200 rpm/10 min); the excess is thrown away. The pellet is then washed twice with 10 ml of 0.9% common salt solution.

Next the pellet is mixed with 0.5 ml of concentrated nitric acid until it has dissolved (about 12 hours). It is then filled with distilled water up to 5 ml. After filtration through a 0.2 micron disposable filter, the manganese content is determined by ICP (Induceley Coupled Plasma).

| | Result: | |
|---|---|---|
| Compound | micrograms manganese/ml | relative take-up |
| Mn-TPPS | 8.4 ± 2.4 | 100 |
| Example 4 | 19.0 ± 1.0 | 226.2 |
| Example 17 | 15.3 ± 0.6 | 182.1 |

The complex compounds according to the invention show a clear superiority in being taken up into the tumor cells compared to the standard Mn-TPPS. In comparison to the latter, the taking up of the compound according to the invention is higher by a factor of 2.26 and 1.82, respectively.

EXAMPLE FOR IN-VIVO NMR DIAGNOSIS

Manganese(III)-[5,10,15,20-tetrakis(4-methoxy-3-sulfonatophenyl)-porphyrin, tetrasodium salt (example 17) was administered i.v. in a dosage of 0.1 mmol/kg to a naked mouse (babl/c nu/nu, female, =20 g) with a subcutaneous HT 29 colon tumor. After dissolving the substance in distilled water, the pH was adjusted to 7.5. The test was performed in a nuclear magnetic tomograph (General Electric Company) with a 2 tesla magnet.

Images were made before and after administration of the contrast medium in the spin-echo sequence ($T_R$=400 msec, $T_E$=30 msec) in the area of the liver and the tumor.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a diagnostic method of conducting magnetic resonance imaging wherein a patient is subjected to said imaging, the improvement comprising administering to said patient a pharmaceutical composition containing a pharmaceutically acceptable carrier and at least one porphyrin compound comprising:

(a) a mesotetraphenylporphyrin ligand of formula I

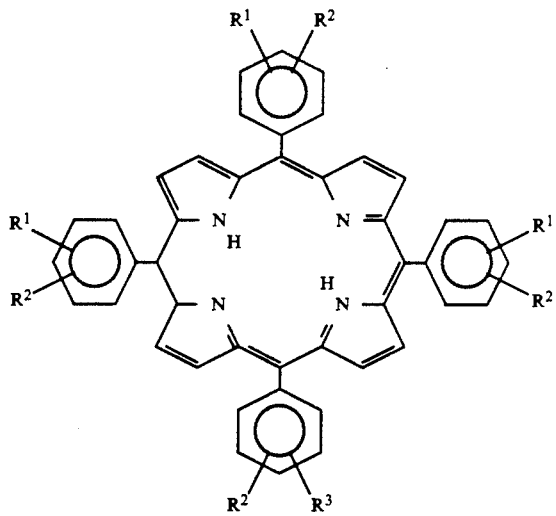

in which $R^1$ is CO—A, $SO_2$—A, $OR^5$, $R^5$, W or NH—W;

A is OH, $OR^4$, $NR^5R^6$ or —$(NH)_x$—{Q—$(NH)_y$}$_w$—W;

$R^4$ is $C_1$-$C_6$-alkyl or benzyl;

$R^5$ and $R^6$ are, independent of one another, hydrogen, saturated, unsaturated, straight-chain, branched-chain or cyclic $C_{1-16}$-hydrocarbon radical optionally substituted by one or more hydroxy or lower alkoxy groups, or when $R^6$ is hydrogen, $R^5$ can be $C_{6-10}$-aryl or $C_{6-10}$-aryl-$C_{1-6}$-alkyl, each optionally substituted by one or more di-$C_1$-$C_6$-alkylamino groups or by one or more $C_1$-$C_6$-alkoxy groups, or $R^5$ and $R^6$, together with the nitrogen atom, can form a saturated or unsaturated 5- or 6-membered ring that optionally contains another nitrogen, oxygen, or sulfur atom or a carbonyl group, and that is optionally substituted by one or more of $C_1$-$C_6$-alkyl, $C_1$-$C_5$-hydroxyalkyl, optionally hydroxylated or $C_1$-$C_6$-alkoxylated $C_2$-$C_6$-alkanoyl, hydroxy, carbamoyl, carbamoyl-$C_1$-$C_6$-alkyl, carbamoyl substituted at the carbamoyl-nitrogen by one or two $C_1$-$C_6$-alkyl groups which can also be linked to form a ring optionally containing an oxygen atom, $C_1$-$C_6$-alkanoylamino, or $C_1$-$C_6$-alkylamino;

x and y each independently is 0, 1 or 2;

w is 0 or 1;

Q is $C_1$-$C_{20}$-alkylene;

W is hydrogen or V—K;

V is a single bond or a straight-chain, branched-chain, cyclic, aliphatic, aromatic or arylaliphatic hydrocarbon radical having up to 20 C atoms optionally containing —NH—, —O—, —S—, —N—, —CO—O—, —O—CO—, (O—CH$_2$CH$_2$—)$_{poly}$, —NH—CO—, —CO—NH—, —NH—NH—, —$C_6H_4$—NH—, —$C_6H_4$—O— or —$C_6H_4$— and optionally substituted by hydroxy, mercapto, imino, epoxy, oxo, thioxo and/or amino group(s);

K is hydrogen or a complexing structure of formula IA, IB, IC or ID

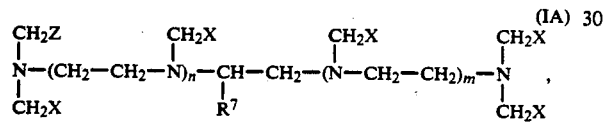

(IA)

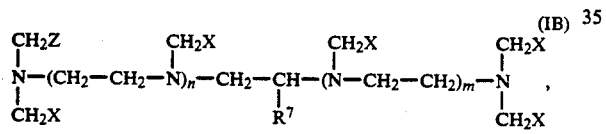

(IB)

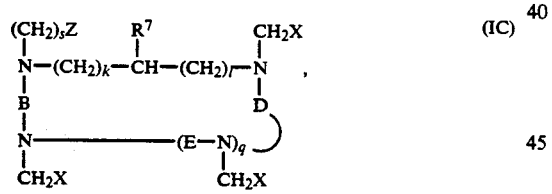

(IC)

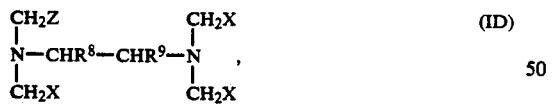

(ID)

n and m each independently is 0, 1, 2, 3, or 4, and n and m together add to no more than 4;

k is 1, 2, 3, 4 or 5;

l is 0, 1, 2, 3, 4 or 5;

q is 0, 1 or 2;

s is 0 or 1;

X is —COOH;

B, D and E, which are the same or different, each are

$R^{10}$ is hydrogen or straight-chain, branched-chain, cyclic, aliphatic, aromatic or arylaliphatic hydrocarbon radical having up to 20 C atoms optionally containing oxygen and/or nitrogen atom(s) and optionally substituted by hydroxy and/or amino group(s);

u is 0, 1, 2, 3, 4 or 5;

v is 0 or 1; and

B, D and E each contain at least 2 and at most 5 carbon atoms in their chain;

Z is

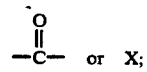

$R^7$ is a direct bond or hydrogen;

$R^8$ and $R^9$ together form dimethylene- or trimethylene-methine, optionally substituted by 1-2 hydroxy or 1-3 $C_1$-$C_4$-alkyl groups, provided that Z is

only when $R^7$ simultaneously is hydrogen and that Z is X only when $R^7$ simultaneously is a direct bond and s is 1;

$R^2$ is hydrogen, fluorine, chlorine, bromine, iodine atom(s), or an $R^1$, $R^4$ or $OR^4$ group;

$R^3$ is one of the groups defined for $R^1$;

wherein said mesotetraphenylporphyrin ligand contains at least one complexing structure K of formulae IA-ID; and wherein a portion of the COOH groups can optionally be present in the ester and/or amide form;

(b) at least one ion of an element of atomic numbers 21-29, 42, 44, or 58-70 which is chelated by a complexing structure K of formulae IA-ID or the porphyrin ring, with the proviso that the porphyrin ring does not chelate a metal ion other than Mn ion; and (c) optionally a cation of a pharmacologically acceptable inorganic and/or organic base, an amino acid, or an amino acid amide.

2. A complex compound comprising a mesotetraphenylporphyrin ligand of formula I

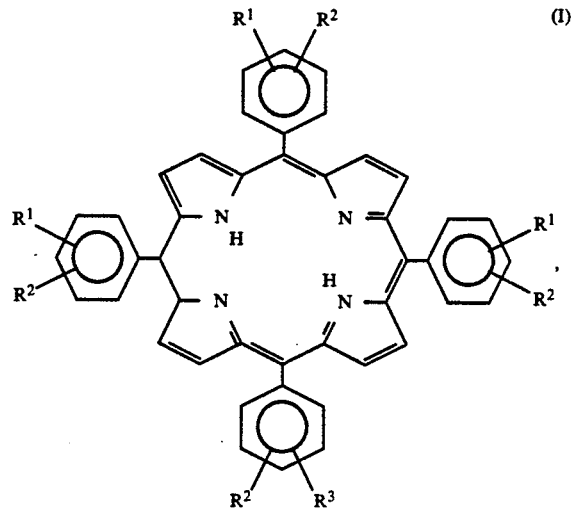

(I)

in which

R¹ is CO—A, SO₂—A, OR⁵, R⁵, W, or NH—W;

A is OH, OR⁴, NR⁵R⁶ or —(NH)$_x$—{Q—(NH)$_y$}$_w$—W;

R⁴ is C₁-C₆-alkyl or benzyl;

R⁵ and R⁶ are, independent of one another, hydrogen, saturated, unsaturated, straight-chain, branched-chain or cyclic C₁₋₁₆-hydrocarbon radical optionally substituted by one or more hydroxy or lower alkoxy groups, or when R⁶ is hydrogen, R⁵ can be C₆₋₁₀-aryl or C₆₋₁₀-aryl-C₁₋₆-alkyl, each optionally substituted by one or more di-C₁-C₆-alkylamino groups or by one or more C₁-C₆-alkoxy groups, or R⁵ and R⁶, together with the nitrogen atom, can form a saturated or unsaturated 5- or 6-membered ring that optionally contains another nitrogen, oxygen, or sulfur atom or a carbonyl group, and that is optionally substituted by one or more of C₁-C₆-alkyl, C₁-C₅-hydroxyalkyl, optionally hydroxylated or C₁-C₆-alkoxylated C₂-C₆-alkanoyl, hydroxy, carbamoyl, carbamoyl-C₁-C₆-alkyl, carbamoyl substituted at the carbamoyl-nitrogen by one or two C₁-C₆-alkyl groups which can also be linked to form a ring optionally containing an oxygen atom, C₁-C₆-alkanoylamino, or C₁-C₆-alkylamino;

x and y each independently is 0, 1 or 2;

w is 0 or 1;

Q is C₁-C₂₀-alkylene;

W is hydrogen or V—K;

V is a single bond or a straight-chain, branched-chain, cyclic, aliphatic, aromatic or arylaliphatic hydrocarbon radical having up to 20 C atoms optionally containing —NH—, —O—, —S—, —N—, —CO—O—, —O—CO—, (O—CH₂CH₂—)$_{poly}$, —NH—CO—, —CO—NH—, —NH—NH—, —C₆H₄—NH—, —C₆H₄—O— or —C₆H₄— and optionally substituted by hydroxy, mercapto, imino, epoxy, oxo, thioxo and/or amino group(s);

K is hydrogen or a complexing structure of formula IA, IB, IC or ID

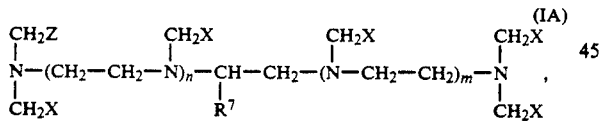

(IA)

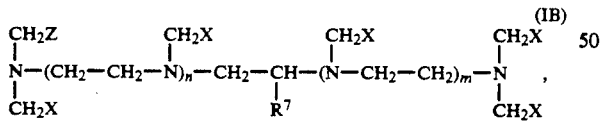

(IB)

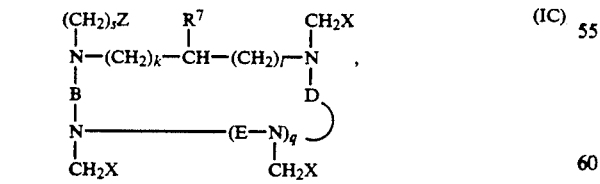

(IC)

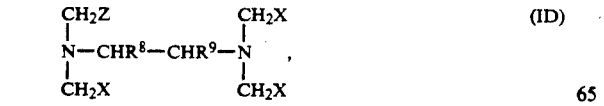

(ID)

n and m each independently is 0, 1, 2, 3, or 4, and n and m together add to no more than 4;

k is 1, 2, 3, 4 or 5;

l is 0, 1, 2, 3, 4 or 5;

q is 0, 1 or 2;

s is 0 or 1;

X is —COOH;

B, D and E, which are the same or different, each is

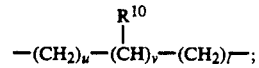

R¹⁰ is hydrogen or straight-chain, branched-chain, cyclic, aliphatic, aromatic or arylaliphatic hydrocarbon radical having up to 20 C atoms optionally containing oxygen and/or nitrogen atom(s) and optionally substituted by hydroxy and/or amino group(s);

u is 0, 1, 2, 3, 4 or 5;

v is 0 or 1; and

B, D and E each contain at least 2 and at most 5 carbon atoms in their chain;

Z is

or X;

R⁷ is a direct bond or hydrogen;

R⁸ and R⁹ together form dimethylene- or trimethylene-methine, optionally substituted by 1-2 hydroxy or 1-3 C₁-C₄-alkyl groups, provided that Z is

only when R⁷ simultaneously is hydrogen and that Z is X only when R⁷ simultaneously is a direct bond and s is 1;

R² is hydrogen, fluorine, chlorine, bromine, iodine atom(s), or an R¹, or R⁴ or OR⁴ group;

R³ is one of the groups defined for R¹;

wherein said mesotetraphenylporphyrin ligand contains at least one complexing structure K of formulae IA–ID; and wherein a portion of the COOH groups can optionally be present in the ester and/or amide form;

and further comprising at least one ion of an element of atomic numbers 13, 21–32, 37–39, 42–44, 49, 50 or 57–83 which is chelated by a complexing structure K of formulae IA–ID or the porphyrin ring, with the proviso that the porphyrin ring does not chelate a metal ion other than the Mn ion;

and optionally comprising a cation of an inorganic and/or organic base, an amino acid, or an amino acid amide.

3. In a method of conducting magnetic resonance imaging, wherein a patient is subjected to said imaging, the improvement comprising administering to said patient a pharmaceutical composition containing:

(a) at least one porphyrin compound comprising a mesotetraphenylporphyrin ligand, wherein at least one of the phenyl groups of said mesotetraphenylporphyrin ligand is substituted by 1 to 2 substituents from the group comprising CO—A, SO$_2$—A, W and NH—W, wherein A is OH, OR$^4$, NR$^5$R$^6$ or —(NH)$_x$—]Q—(NH)$_y$]$_w$—W, R$^4$ is C$_1$-C$_6$-alkyl or benzyl, R$^5$ and R$^6$ are, independent of one another, hydrogen, saturated, unsaturated, straight-chain, branched-chained or cyclic C$_{1-16}$-hydrocarbon radical optionally substituted by one or more hydroxy or lower alkoxy groups, or when R$^6$ is hydrogen, R$^5$ can be C$_{6-10}$-aryl or C$_{6-10}$-aryl-C$_{1-6}$-alkyl, each optionally substituted by one or more di-C$_1$-C$_6$-alkylamino groups or by one or more C$_1$-C$_6$-alkoxy groups, or R$^5$ and R$^6$, together with the nitrogen atom, can form a saturated or unsaturated 5- or 6-membered ring that optionally contains another nitrogen, oxygen, or sulfur atom or a carbonyl group, and that is optionally substituted by one or more of C$_1$-C$_6$-alkyl, C$_1$-C$_5$-hydroxyalkyl, optionally hydroxylated or C$_1$-C$_6$-alkoxylated C$_2$-C$_6$-alkanoyl, hydroxy, carbamoyl, carbamoyl-C$_1$-C$_6$-alkyl, carbamoyl substituted at the carbamoyl-nitrogen by one or two C$_1$-C$_6$-alkyl groups which can also be linked to form a ring optionally containing an oxygen atom, C$_1$-C$_6$-alkanoylamino, or C$_1$-C$_6$-alkylamino;

x and y are independently 0, 1, or 2;

w is 0 or 1;

Q is C$_{1-20}$-alkylene;

W is hydrogen or V-K;

V is a single bond or a straight-chain, branched-chain, cyclic, aliphatic, aromatic or arylaliphatic hydrocarbon radical having up to 20 C atoms optionally containing —NH—, —O—, —S—, —N—, —CO—O—, —O—CO—, (O—CH$_2$CH$_2$—)$_{poly}$, —NH—CO—, —CO—NH—, —NH—NH—, —C$_6$H$_4$—NH—, —C$_6$H$_4$—O— or —C$_6$H$_4$— and optionally substituted by hydroxy, mercapto, imino, epoxy, oxo, thioxo and/or amino group(s);

K is hydrogen or a complexing structure of formula IA, IB, IC or ID

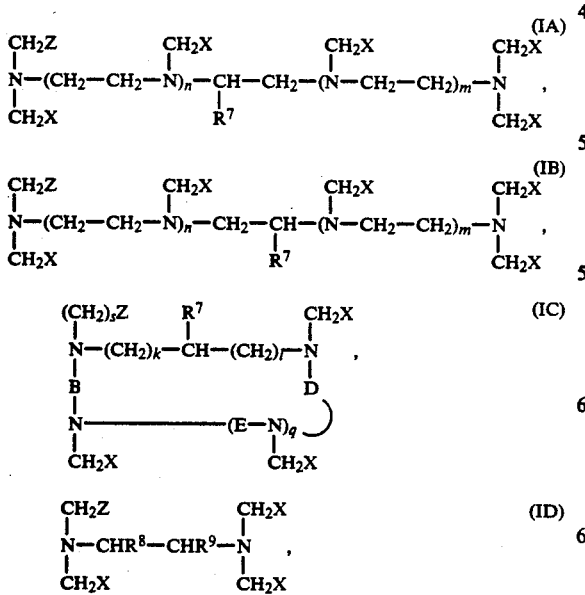

n and m each independently is 0, 1, 2, 3, or 4, and n and m together add to no more than 4;

k is 1, 2, 3, 4 or 5;

l is 0, 1, 2, 3, 4 or 5;

q is 0, 1, or 2;

s is 0 or 1;

X is —COOH;

B, D and E, which are the same or different, each are

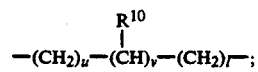

R$^{10}$ is hydrogen or straight-chain, branched-chain, cyclic aliphatic, aromatic or arylaliphatic hydrocarbon radical having up to 20 C atoms optionally containing oxygen and/or nitrogen atom(s) and optionally substituted by hydroxy and/or amino groups(3);

u is 0, 1, 2, 3, 4 or 5;

v is 0 or 1; and

B, D and E each contain at least 2 and at most 5 carbon atoms in their chain;

Z is

or X;

R$^7$ is a direct bond or hydrogen;

R$^8$ and R$^9$ together form dimethylene- or trimethylene-methine, optionally substituted by 1-2 hydroxy or 1-3 C$_1$-C$_4$-alkyl groups, provided that Z is

only when R$^7$ simultaneously is hydrogen and than Z is X only when wherein said mesotetraphenylporphyrin ligand contains at least one complexing structure K of formula IA-ID; and R$^7$ simultaneously is a direct bond and s is 1;

wherein a portion of the COOH groups can optionally be present in the ester and/or amide form; and said porphyrin compound further contains at least one ion of an element of atomic numbers 21-29, 42, 44, or 58-70 which is chelated by a complexing structure K of formulae IA-ID the porphyrin ring, with the proviso that the porphyrin ring does not chelate a metal ion other than the Mn ion, and optionally a cation of a pharmacologically acceptable inorganic and/or organic base, an amino acid, or an amino acid amine; and (b) a pharmaceutically acceptable carrier.

4. A method according to claim 1, wherein said pharmaceutical composition is sterile.

5. A method according to claim 1, wherein said pharmaceutical composition further comprises at least one separate complexing agent.

6. A method according to claim 1, wherein said pharmaceutical composition is administered in doses amounting to 0.1 micromole-1 mmole of said complex per kg of body weight.

7. A method according to claim 1, wherein said pharmaceutical composition is administered enterally or parenterally.

8. A method according to claim 1, wherein said element is Mn, Gd, Dy, and Yb.

9. A method according to claim 1, wherein said element is Gd.

10. A method according to claim 1, wherein said element is Mn.

11. A method according to claim 1, wherein said at least one porphyrin compound is water-soluble.

12. A method according to claim 3, wherein said at least one porphyrin compound is water-soluble.

13. A method of enhancing NMR imageability of a patient comprising administering to the patient, in an amount effective to enhance NMR image contrast, a physiologically compatible chelate complex of a paramagnetic ion, wherein said complex is a complex according to claim 9.

14. A method according to claim 13, wherein said chelate complex is water-soluble.

15. A method according to claim 1, wherein at least one of $R^1$, $R^2$, and $R^3$ is CO—A or $SO_2$—A.

16. A method according to claim 1, wherein at least one of $R^1$, $R^2$, and $R^3$ is W or NH—W.

17. A method according to claim 15, wherein A is $NR^5R^6$.

18. A method according to claim 15, wherein A is —$(NH)_x$—[Q—$(NH)_y]_w$—W.

19. A method according to claim 1, wherein $R^2$ is F.

20. A method according to claim 1, wherein said porphyrin compound is in the form of a salt with an inorganic and/or organic base, amino acid, or amino acid amide.

21. A method according to claim 16, wherein said porphyrin compound is in the form of a salt with an inorganic and/or organic base, amino acid, or amino acid amide.

22. A method of claim 13, wherein V is —$(CH_2)_2NH$; —$CH_2$—O—$C_6H_4$—$CH_2$; —$CH_2$—CH(OH)—$CH_2$O—$C_6H_4$—$CH_2$; —C(=NH)—O—$C_6H_4$—$CH_2$; —$(CH_2)_4$—NH—CO—$CH_2$—O—$C_6H_4$—$CH_2$; —$(CH_2)_4$—NH—$CH_2$—CH(OH)—$CH_2$—O—$C_6H_4$—$CH_2$; —$(CH_2)_3$—O—$C_6H_4$—$CH_2$; —$CH_2$—CO—NH—$(CH_2)_3$—O—$CH_2$; —$CH_2$—CO—NH—$CH_2$—NH; —$CH_2$—CO—NH—$(CH_2)_2$; —$CH_2CO$—NH$(CH_2)_{10}$; —$CH_2$—CO—NH—$(CH_2)_2$—S; —$(CH_2)_4$—NH—CO—$(CH_2)_8$; —$CH_2CO$—NH—$(CH_2)_3$—NH; —$(CH_2)_3$—NH; —$(CH_2)$—NH—C(=S)—NH—$C_6H_4$—$CH_2$; or —$(CH_2)_2$—NH—CO—$CH_2$—$(OCH_2CH_2)_{43}$—$OCH_2$.

23. A composition according to claim 17, containing at least one ion of an element of atomic numbers 21–29, 42, 44 or 57–83.

24. A composition according to claim 17, containing at least one ion of an element of atomic numbers 13, 27, 29, 31, 32, 37–39, 43, 49, 62, 64, 70 or 77.

25. A compound according to claim 2, containing at least one ion of an element of atomic numbers 21–29, 42, 44 or 57–83.

26. A compound according to claim 2, containing at least one ion of an element of atomic numbers 13, 27, 29, 31, 32, 37–39, 43, 49, 62, 64, 70 or 77.

27. In a diagnostic method of magnetic resonance imaging wherein a patient is subjected to said imaging, the improvement comprising administering to said patient manganese(III)-[5,10,15,20-tetrakis(4-methoxy-3-sulfonatophenyl)-prophyryin]-acetate, tetrasodium salt.

28. A method according to claim 1, wherein $R^5$ and $R^6$ together with the nitrogen R atom, are pyrrolidinyl, piperidyl, pyrazolidinyl, pyrrolinyl, pyrazolinyl, piperazinyl, morpholinyl, imidazolidinyl, oxazolidinyl or thiazolidinyl.

29. A method according to claim 1, wherein V is a single bond or a straight-chain, branched, or cyclic aliphatic, aromatic or arylaliphatic group having up to 20 carbons and optionally containing —NH—, —O—, —S—, —N—, —CO—O—, —O—CO—, (O—$CH_2C$-$H_2$—)$_{poly}$, —NH—CO—, —CO—NH—, —N-H—NH—, —$C_6H_4$—NH—, —$C_6H_4$—O—, or —$C_6$-$H_4$— groups.

30. A method according to claim 1, wherein
$R^5$ and $R^6$ are each, independent of one another, hydrogen or saturated, unsaturated, straight-chain, branched-chain or cyclic $C_{1-16}$hydrocarbon radical optionally substituted by one or more hydroxy or lower alkoxy groups, or when $R^6$ is hydrogen, $R^5$ can also be $C_{6-10}$-aryl or $C_{6-10}$aryl-$C_{1-6}$-alkyl, each being optionally substituted by one or more di-$C_1$-$C_6$-alkylamino groups or by one or more $C_1$-$C_6$-alkoxy groups, or, p1 $R^5$ and $R^6$, together with the nitrogen atom, are pyrrolidinyl, piperidyl, pyrazolidinyl, pyrrolinyl, pyrazolinyl, piperazinyl, morpholinyl, imidazolidinyl, oxazolidinyl or thiazolidinyl, in each case being optionally substituted by one or more of $C_1$-$C_6$-alkyl, $C_1$-$C_5$-hydroxyalkyl, $C_2$-$C_6$-alkanoyl, hydroxylated $C_2$-$C_6$-alkanoyl, $C_1$-$C_6$-alkoxylated $C_2$-$C_6$-alkanoyl, hydroxy, carbamoyl, carbamoyl-$C_1$-$C_6$-alkyl, carbamoyl substituted at the carbamoyl-nitrogen by one or two $C_1$-$C_6$-alkyl groups which can also be linked to form a ring optionally containing an oxygen atom, $C_1$-$C_6$-alkanoylamino, or $C_1$-$C_6$-alkylamino; and is a single bond or a straight-chain, branched, or cyclic aliphatic, aromatic or arylaliphatic group having up to 20 carbons and optionally containing —NH—, —O—, —S—, —N—, —CO—O—, —O—CO—, (O—$CH_2CH_2$—)$_{poly}$, —NH—CO—, —CO—NH—, —NH—NH—, —$C_6H_4$—NH—, —$C_6H_4$—O—, or —$C_6H_4$— groups.

31. A method according to claim 1, wherein said porphyrin compound is:
mesotetrakis{4-[1-carboxylato-2,5,8-tris(carboxylatomethyl)-2,5,8-triazanonyl-carbonylamino]-phenyl}-porphyrin, gadolinium(III)-complex, tetrasodium salt;
manganese(III)-{mesotetrakis-[4-(1-carboxylato-2,5,8-tris(carboxylatomethyl)-2,5,8-triazanonyl-carbonylamino)-phenyl]-porphyrin}-acetate, gadolinium complex, tetrasodium salt;
5-{4-[1-carboxylato-10 -oxo-2,5,8-tris(carboxylatomethyl)-2,5,8,11-tetraazatridecylcarbamoyl]-phenyl}-10,15,20-tris-(4-carboxylatophenyl)-porphyrin, gadolinium complex, tetrasodium salt;
manganese(III)-{5-[4-(1-carboxylate-10-oxo-2,5,8-tris(carboxylatomethyl)-2,5,8,11-tetraazatridecyl-carbamoyl)-phenyl]-10,15,20-tris-(4-carboxylatophenyl)-porphyrin}-acetate, gadolinium complex, tetrasodium salt;
manganese(III)-{5-[4-(1-carboxylato-10-oxo-2,5,8-tris-(carboxylatomethyl)-2,5,8,11-tetraazatridecyl-carbamonyl)-phenyl]-10,15,20-tris-(4-carboxylatophenyl)-porphyrin}-acetate, heptasodium salt;
5-{4-[1-carboxylato-10-oxo-2,5,8-tris(carboxylatomethyl)-2,5,8,11-tetraazatridecylcarbamoyl]-phenyl}-

10,15,20-tris-(4-carboxylatophenyl)-porphyrin, dysprosium complex, tetrasodium salt;

mesotetrakis-{4-[1-carboxylato-2,5,8-tris(carboxylatomethyl)-2,5,8-triazanonyl-carbonylamino]-phenyl}-porphyrin, ytterbium complex, tetrasodium salt;

5-{4-[3-[4-(1-carboxylato-2,5-bis(carboxylatomethyl)-6-[N,N-bis(carboxylatomethyl)-aminomethyl]-2,5-diazaheptyl)-phenyl]-thioureidoethylcarbamoyl]-phenyl}-10,15,20-tris-(4-carboxylatophenyl)-porphyrin, gadolinium complex, pentasodium salt;

5-{4-[4,7,10-tris(carboxylatomethyl)-1,4,7,10-tetraazacyclododecan-1-yl-methylcarbonylaminoethylcarbamoyl]-phenyl{-10,15,20-tris-(4-carboxylatophenyl)-porphyrin, gadolinium complex, trisodium salt;

manganese(III)-{5-[4-[4,7,10-tris(carboxylatomethyl)-1,4,7,10-tetraazacyclododecan-1-ylcarbonyl]-phenyl]-10,15,20-tris-(4-carboxylatophenyl)-porphyrin}-acetate, hexasodium salt;

5,10,15-tris-{4-[1-carboxylato-10-oxo-2,5,8-tris(carboxylatomethyl)-2,5,8,11-tetraazatridecylcarbamoyl]- phenyl}-20-(4-carboxylatophenyl)-porphyrin, gadolinium complex, tetrasodium salt;

mesotetrakis-{4-[1-carboxylato-10-oxo-2,5,8-tris(carboxylatomethyl)-2,5,8,11-tetraazatridecylcarbamoyl]-phenyl}-porphyrin, gadolinium complex, tetrasodium salt;

manganese(III)-{mesotetrakis-[4-(1-carboxylato-10-oxo-2,5,8,-tris(carboxylatomethyl)-2,5,8,11-tetraazatridecylcarbamoyl)-phenyl]-porphyrin}-acetate, gadolinium complex, tetrasodium salt;

mesotetrakis-{3-[1-carboxylato-2,5,8-tris(carboxylatomethyl)-2,5,8-triazanonylcarbonylamino]-4-methylphenyl}-porphyrin, gadolinium complex, tetrasodium salt; or manganese(III)-{mesotetrakis-[3-[1-carboxylato2,5,8-tris(carboxylatomethyl)-2,5,8-triazanonylcarbonylmethyl]-4-methylphenyl]-porphyrin}-actate, gadolinium complex, tetrasodium salt.

32. A method according to claim 1, wherein said mesotetraphenylporphyrin ligand is:

mesotetrakis{4-[1-carboxylato-2,5,8-tris(carboxylatomethyl)-2,5,8-triazanonyl-carbonylamino]-phenyl}-porphyrin;

5-{4-[1-carboxylato-10-oxo-2,5,8-tris(carboxylatomethyl)-2,5,8,11-tetraazatridecylcarbamonyl]-phenyl}-10,15,20-tris-(4-carboxylatophenyl)-porphyrin;

5-{4-[3-[4-(1-carboxylato-2,5-bis(carboxylatomethyl)-6-[N,N-bis(carboxylatomethyl)-aminomethyl]-2,5-diazaheptyl)-phenyl]-thioureidoethylcarbamoyl]-phenyl}-10,15,20-tris-(4-carboxylatophenyl)-porphyrin;

5-{4-[4,7,10-tris(carboxylatomethyl)-1,4,7,10-tetraazacyclododecan-1-yl-methylcarbonylaminoethylcarbamoyl]-phenyl}-10,15,20-tris-(4-carboxylatophenyl)-porphyrin;

5,10,15-tris-{4-[1-carboxylato-10-oxo-2,5,8-tris(carboxylatomethyl)-2,5,8,11-tetraazatridecylcarbamoyl]-phenyl}-20-(4-carboxylatophenyl)-porphyrin;

mesotetrakis-{4-[1-carboxylato-10-oxo-2,5,8-tris(carboxylatomethyl)-2,5,8,11tetraazatridecylcarbamoyl]-phenyl}-porphyrin; or mesotetrakis-{3-[1-carboxylato-2,5,8-tris(carboxylatomethyl)-2,5,8-triazanonylcarbonylamino]-4-methylphenyl}-porphyrin.

33. A pharmaceutical composition comprising:
(a) at least one porphyrin compound having a mesotetraphenylporphyrin ligand of formula I

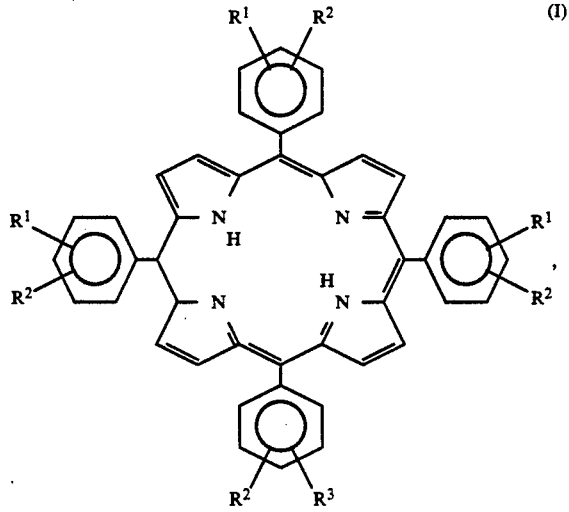

in which
$R^1$ is CO—A, $SO_2$—A, $OR^5$, $R^5$, W or NH—W;
A is OH, $OR^4$, $NR^5R^6$ or —$(NH)_x$—{Q—$(NH)_y$}$_w$—W;
$R^4$ is $C_1$—$C_6$-alkyl or benzyl;
$R^5$ and $R^6$ are, independent of one another, hydrogen, saturated, unsaturated, straight-chain, branched-chain or cyclic $C_{1-16}$-hydrocarbon radical optionally substituted by one or more hydroxy or lower alkoxy groups, or when $R^6$ is hydrogen, $R^5$ can be $C_{6-10}$-aryl or $C_{6-10}$-aryl-$C_{1-6}$-alkyl, each optionally substituted by one or more di-$C_1$-$C_6$-alkylamino groups or by one or more $C_1$-$C_6$-alkoxy groups, or
$R^5$ and $R^6$, together with the nitrogen atom, can form a saturated or unsaturated 5- or 6-membered ring that optionally contains another nitrogen, oxygen, or sulfur atom or a carbonyl group, and that is optionally substituted by one or more of $C_1$-$C_6$-alkyl, $C_1$-$C_5$-hydroxyalkyl, optionally hydroxylated or $C_1$-$C_6$-alkoxylated $C_2$-$C_6$-alkanoyl, hydroxy, carbamoyl, carbamoyl-$C_1$-$C_6$-alkyl, carbamoyl substituted at the carbamoyl-nitrogen by one or two $C_1$-$C_6$-alkyl groups which can also be linked to form a ring optionally containing an oxygen atom, $C_1$-$C_6$-alkanoylamino, or $C_1$-$C_6$-alkylamino;
x and y each independently is 0, 1 or 2;
w is 0 or 1;
Q is $C_1$-$C_{20}$-alkylene;
W is hydrogen or V-K;
V is a single bond or a straight-chain, branched-chain, cyclic, aliphatic, aromatic or arylaliphatic hydrocarbon radical having up to 20 C atoms optionally containing —NH—, —O—, —S—, —N—, —CO—O—, —O—CO—, (O—$CH_2CH_2$—)$_{poly}$, —NH—CO—, —CO—NH—, —NH—NH—, —$C_6H_4$—NH—, —$C_6H_4$—O— or —$C_6H_4$— and optionally substituted by hydroxy, mercapto, imino, epoxy, oxo, thioxo and/or amino group(s);
K is hydrogen or a complexing structure of formula IA, IB, IC or ID $$\begin{array}{c}
\text{CH}_2\text{Z} \quad\quad \text{CH}_2\text{X} \quad\quad \text{CH}_2\text{X} \quad\quad \text{CH}_2\text{X} \\
| \quad\quad\quad | \quad\quad\quad | \quad\quad\quad | \\
\text{N}-(\text{CH}_2-\text{CH}_2-\text{N})_n-\text{CH}-\text{CH}_2-(\text{N}-\text{CH}_2-\text{CH}_2)_m-\text{N} \\
| \quad\quad\quad\quad\quad\quad\quad\quad | \quad\quad\quad\quad\quad\quad\quad | \\
\text{CH}_2\text{X} \quad\quad\quad\quad\quad\quad \text{R}^7 \quad\quad\quad\quad\quad\quad \text{CH}_2\text{X}
\end{array} \quad (\text{IA})$$

$$\begin{array}{c}
\text{CH}_2\text{Z} \quad\quad \text{CH}_2\text{X} \quad\quad \text{CH}_2\text{X} \quad\quad \text{CH}_2\text{X} \\
| \quad\quad\quad | \quad\quad\quad | \quad\quad\quad | \\
\text{N}-(\text{CH}_2-\text{CH}_2-\text{N})_n-\text{CH}_2-\text{CH}-(\text{N}-\text{CH}_2-\text{CH}_2)_m-\text{N} \\
| \quad\quad\quad\quad\quad\quad\quad\quad | \quad\quad\quad\quad\quad\quad\quad | \\
\text{CH}_2\text{X} \quad\quad\quad\quad\quad\quad \text{R}^7 \quad\quad\quad\quad\quad\quad \text{CH}_2\text{X}
\end{array} \quad (\text{IB})$$

$$\begin{array}{c}
(\text{CH}_2)_s\text{Z} \quad \text{R}^7 \quad\quad\quad \text{CH}_2\text{X} \\
| \quad\quad\quad | \quad\quad\quad\quad | \\
\text{N}-(\text{CH}_2)_k-\text{CH}-(\text{CH}_2)_l-\text{N} \\
| \quad\quad\quad\quad\quad\quad\quad\quad\quad\quad | \\
\text{B} \quad\quad\quad\quad\quad\quad\quad\quad\quad \text{D} \\
| \quad\quad\quad\quad\quad\quad\quad\quad\quad\quad | \\
\text{N}-\!\!-\!\!-\!\!-\!\!-\!\!-\!\!-(\text{E}-\text{N})_q \!\!\!\!\!\!\!\!\!\!\!\!\!\!\!\!\!\! \\
| \quad\quad\quad\quad\quad\quad\quad\quad\quad\quad | \\
\text{CH}_2\text{X} \quad\quad\quad\quad\quad\quad \text{CH}_2\text{X}
\end{array} \quad (\text{IC})$$

$$\begin{array}{c}
\text{CH}_2\text{Z} \quad\quad\quad\quad \text{CH}_2\text{X} \\
| \quad\quad\quad\quad\quad\quad\quad | \\
\text{N}-\text{CHR}^8-\text{CHR}^9-\text{N} \\
| \quad\quad\quad\quad\quad\quad\quad | \\
\text{CH}_2\text{X} \quad\quad\quad\quad \text{CH}_2\text{X}
\end{array} \quad (\text{ID})$$

n and m each independently is 0, 1, 2, 3, or 4, and n and m together add to no more than 4;

k is 1, 2, 3, 4 or 5;

l is 0, 1, 2, 3, 4 or 5;

q is 0, 1 or 2;

s is 0 or 1;

X is —COOH;

B, D and E, which are the same or different, each are $$-(\text{CH}_2)_u - \overset{\text{R}^{10}}{\underset{|}{(\text{CH})}}_v - (\text{CH}_2)_r-;$$

$R^{10}$ is hydrogen or straight-chain, branched-chain, cyclic, aliphatic, aromatic or arylaliphatic hydrocarbon radical having up to 20 C atoms optionally containing oxygen and/or nitrogen atom(s) and optionally substituted by hydroxy and/or amino group(s);

u is 0, 1, 2, 3, 4 or 5;

v is 0 or 1;

B, D and E each contain at least 2 and at most 5 carbon atoms in their chain;

Z is $$-\overset{\text{O}}{\underset{}{\overset{\|}{\text{C}}}}-$$

or X;

$R^7$ is a direct bond or hydrogen;

$R^8$ and $R^9$ together form dimethylene- or trimethylene-methine, optionally substituted by 1-2 hydroxy or 1-3 $C_1$-$C_4$-alkyl groups, provided that Z is $$-\overset{\text{O}}{\underset{}{\overset{\|}{\text{C}}}}-$$

only when $R^7$ simultaneously is hydrogen and that Z is X only when $R^7$ simultaneously is a direct bond and s is 1;

$R^2$ is hydrogen, fluorine, chlorine, bromine, iodine atom(s), or an $R^1$, $R^4$ or $OR^4$ group;

$R^3$ is one of the groups defined for $R^1$;

and wherein said mesotetraphenylporphyrin ligand contains at least one complexing structure K of formulae IA-ID wherein a portion of the COOH groups can optionally be present in the ester and/or amide form;

and further comprising at least one ion of an element of atomic numbers 13, 21-32, 37-39, 42-44, 49, 50 or 57-83 which is chelated by a complexing structure K of formulae IA-ID or the porphyrin ring, with the proviso that the porphyrin ring does not chelate a metal ion other than the Mn ion;

and optionally comprising a cation of an inorganic and/or organic base, an amino acid or an amino acid amide; and (b) a pharmaceutically acceptable carrier.

* * * * *